United States Patent
Li et al.

(10) Patent No.: US 10,274,499 B2
(45) Date of Patent: Apr. 30, 2019

(54) SH2 DOMAIN VARIANTS

(71) Applicants: THE UNIVERSITY OF WESTERN ONTARIO, London (CA); THE GOVERNING COUNCIL OF THE UNIVERSITY OF TORONTO, Toronto (CA)

(72) Inventors: Shun-Cheng Li, London (CA); Tomonori Kaneko, London (CA); Xuan Cao, London (CA); Sachdev Singh Sidhu, Toronto (CA); Haiming Huang, Toronto (CA)

(73) Assignees: THE UNIVERSITY OF WESTERN ONTARIO, London (CA); THE GOVERNING COUNCIL OF THE UNIVERSITY OF TORONTO, Toronto (CA)

(*) Notice: Subject to any disclaimer, the term of this patent is extended or adjusted under 35 U.S.C. 154(b) by 0 days.

(21) Appl. No.: 14/388,592

(22) PCT Filed: Mar. 27, 2013

(86) PCT No.: PCT/CA2013/000279
§ 371 (c)(1),
(2) Date: Sep. 26, 2014

(87) PCT Pub. No.: WO2013/142965
PCT Pub. Date: Oct. 3, 2013

(65) Prior Publication Data
US 2015/0177258 A1 Jun. 25, 2015

Related U.S. Application Data

(60) Provisional application No. 61/616,167, filed on Mar. 27, 2012.

(51) Int. Cl.
| | | |
|---|---|---|
| *C07K 14/47* | (2006.01) | |
| *G01N 33/68* | (2006.01) | |
| *C07K 1/22* | (2006.01) | |
| *A61K 38/17* | (2006.01) | |
| *G01N 21/64* | (2006.01) | |

(52) U.S. Cl.
CPC .......... *G01N 33/6812* (2013.01); *C07K 1/22* (2013.01); *C07K 14/47* (2013.01); *G01N 33/6842* (2013.01); *A61K 38/1709* (2013.01); *G01N 2440/14* (2013.01)

(58) Field of Classification Search
None
See application file for complete search history.

(56) References Cited

U.S. PATENT DOCUMENTS

| | | | |
|---|---|---|---|
| 4,609,893 A | 9/1986 | Cornish et al. | |
| 4,713,325 A | 12/1987 | Lutz et al. | |
| 4,714,681 A | 12/1987 | Reading et al. | |
| 4,716,111 A | 12/1987 | Osband et al. | |
| 4,716,117 A | 12/1987 | Kuo et al. | |
| 4,720,459 A | 1/1988 | Winkelhake et al. | |
| 5,786,454 A | 7/1998 | Waksman et al. | |
| 5,843,456 A | 12/1998 | Paoletti et al. | |
| 5,869,270 A | 2/1999 | Rhode et al. | |
| 6,824,989 B1 | 11/2004 | Eisinger et al. | |
| 7,846,746 B2 | 12/2010 | Nollau et al. | |

FOREIGN PATENT DOCUMENTS

WO 2011130343 A1 10/2011

OTHER PUBLICATIONS

Waksman et al., Crystal structure of the phosphotyrosine recognition domain of v-src complexed with tyrosine-phosphorylated peptides, Nature, 1992, 358, 646-53.*
Campbell et al., Diversity in the SH2 domain family phosphotyrosyl peptide binding site, Protein Eng., 2003, 16, 217-27.*
Bradshaw et al., Investigation of phosphotyrosine recognition by the SH2 domain of the SrC Kinase, J. Mol. Biol., 1999, 293, 971-85.*
Guo et al., Protein tolerance to random amino acid change, Proc. Natl. Acad. Sci. USA, 2004, 101, 9205-10.*
Genbank, Accession No. NP_002077, 2010, www.ncbi.nlm.gov.*
Eck, Michael J. et al Recognization of a high-affinity phosphotyrosyl peptide by the Src homology-2 domain of p56, Nature, Mar. 4 1993, p. 87-91, v362, Nature Publishing Group.
Kimber, Matthew S. et al. Structural Basis for Specificity Switching of the Src SH2 Domain, Molecular Cell, Jun. 2000, p. 1043-1049, v5, Cell Press.
Liu, Bernard A. et al. The Human and Mouse Complement of SH2 Domain Proteins-Establishing the Boundaries of Phosphotyrosine Signaling, Molecular Cell, Jun. 23 2006, p. 851-868, v22, Elsevier Inc.
Hino, Nobymasa et al. Genetic Incorporation of Photo-Crosslinkable Amino Acid Reveals Novel Protein Complexes with GRB2 in Mammalian Cells, J. Mol. Biol., 2011, p. 343-353, v406, Elsevier Ltd.

(Continued)

*Primary Examiner* — Robert B Mondesi
*Assistant Examiner* — Todd M Epstein

(57) ABSTRACT

The present invention relates to variant SH2 domains for binding a phosphotyrosine (pTyr)-containing peptide. The variant SH2 domains of the present invention include a parent SH2 domain having at least one amino acid substitution in a pre-defined region of 15 amino acid positions of the parent SR2 domain, wherein said at least one amino acid substitution increases the affinity of the variant SH2 domain for the pTyr-containing peptide relative to the parent SH2 domain. The present application relates also to methods of using the variant SH2 domains in the treatment of protein kinase-associated disorders, or the diagnosis or prognosis of protein kinase-associated disorders, for isolating and measuring the concentration of pTyr-containing molecules, and as reagents in research.

9 Claims, 18 Drawing Sheets
Specification includes a Sequence Listing.

(56) References Cited

OTHER PUBLICATIONS

Gunther, Ulrich L. et al. Nuclear Magnetic Resonance Structure of the P395S Mutant of the N-SH2 Domain of the p85 Subunit of PI3 Kinase: An SH2 Domain with Altered Specificity, Biochemistry, 2003, p. 11120-11127, v42, American Chemical Society.
Bradshaw, J. Michael, et al. Investigation of Phosphotyrosine Recognition by the SH2 Domain of the Src Kinase, J. Mol. Biol., 1999, p. 971-985, v293.
Kaneko, Tomonori et al. Loops Govern SH2 Domain Specificity by Controlling Access to Binding Pockets, Sci. Signal, May 4, 2010, p. 1-17, v3, issue 120.

* cited by examiner

```
FYN_HUMAN (149)  WYFGKLGRKDAERQLLSFGNPRGTFLIRESETTKGAYSLSIRDWDDMKGDHVKHYKIRKLDNG
SRC_HUMAN (151)  WYFGKITRRESERLLLNAENPRGTFLVRESETTKGAYCLSVSDPDNAKGLNVKHYKIRKLDSG
GRB2_HUMAN (60)  WFFGKIPRAKAEDMLSKQR-HDGAFLIRESESAPGDFSLSVKFGND-----VQHFKVLRDGAG
                 Position  1  2  3     4  5  6  7  8  9 10 11 12 13 14 15
```

(b)

| Position | Protein residue number |
|---|---|
| 4 | i (identified from a multiple sequence alignment) |
| 5 | i + 2 |
| 6 | i + 3 |
| 7 | i + 4 |
| 8 | i + 5 |

(c)

| Position | Numbering system defined by Eck, Shoelson & Harrison (1993) *Nature*, Vol. 362, 87-91 |
|---|---|
| 1 | αA2 |
| 2 | αA3 |
| 3 | αA5 |
| 4 | βB5 |
| 5 | βB7 |
| 6 | βC1 |
| 7 | βC2 |
| 8 | βC3 |
| 9 | βC1 |
| 10 | βC3 |
| 11 | βC4 |
| 12 | βC5 |
| 13 | βD3 |
| 14 | βD4 |
| 15 | βD6 |

| pTyr peptide | Sequence | Notes |
|---|---|---|
| | (The symbol "a" denotes a 6-aminohexanoic acid linker.) | |
| *pTyr+2 Asn group peptide* | | |
| VEGFR1-pY1213 | biotin-a-a-D-V-R-pY-V-N-A-A-K-F-amide | Modified from the Wt sequence: DVRpYVNAFKF |
| ShcA-pY239 | biotin-a-a-D-H-Q-pY-Y-N-D-A-P-G-amide | Modified from the Wt sequence: DHQpYYNDFPG |
| β2-adrenoreceptor-pY350 | biotin-a-a-S-K-A-pY-G-N-G-A-S-S-amide | Modified from the Wt sequence: KApYGNGYSS |
| PDGFRβ-pY716 | biotin-a-a-A-E-L-pY-S-N-A-A-P-V-amide | Modified from the Wt sequence: AELpYSNALPV |
| ErbB2-pY1139 | biotin-a-a-Q-P-E-pY-V-N-Q-A-D-V-amide | Modified from the Wt sequence: QPEpYVNQPDV |
| TIE2-pY1102 | biotin-a-a-R-K-T-pY-V-N-T-T-L-Y-amide | |
| | | |
| *pTyr+3 Leu/Ile group peptide* | | |
| HaPyV MidT-pY324mod | biotin-a-E-P-Q-pY-E-E-I-E-E-amide | Modified from the Wt sequence: EPQpYEEIPI |
| FCERB-pY219 | biotin-a-a-D-R-V-pY-E-E-L-N-I-Y-S-amide | |
| SIG11-pY668 | biotin-a-a-T-T-E-pY-S-E-I-K-I-H-T-amide | |
| CD79A-pY188 | biotin-a-a-E-N-L-pY-E-G-L-N-L-D-D-amide | |
| CEA20-pY578 | biotin-a-a-E-S-I-pY-E-V-L-G-M-Q-Q-amide | |
| | | |
| *pTyr+4 Leu/Ile group peptide* | | |
| TRAF7-pY275 | biotin-a-a-Q-D-T-pY-E-T-B-L-E-T-amide | Not a known physiological phosphorylation site |
| MALT1-pY470 | biotin-a-a-R-N-D-pY-D-D-T-I-P-I-amide | Not a known physiological phosphorylation site |
| RSKL-pY423 | biotin-a-a-Y-Q-H-pY-D-L-D-L-K-D-amide | |
| B-raf-pY85 | biotin-a-a-Y-E-E-pY-T-S-K-L-D-A-amide | Not a known physiological phosphorylation site |
| | | |
| *EGFR pTyr sites* | | |
| EGFR-pY869 | biotin-a-a-E-K-E-pY-H-A-E-G-G-K-amide | |
| EGFR-pY915 | biotin-a-a-S-K-P-pY-D-G-I-P-A-S-amide | |
| EGFR-pY944 | biotin-a-a-I-D-V-pY-M-I-M-V-K-A-amide | Modified from the Wt sequence: IDVpYMIMVKC |
| EGFR-pY978 | biotin-a-a-P-Q-R-pY-L-V-I-Q-G-D-amide | |
| EGFR-pY998 | biotin-a-a-S-N-F-pY-R-A-L-M-D-E-amide | |
| EGFR-pY1016 | biotin-a-a-A-D-E-pY-L-I-P-Q-Q-G-amide | |
| EGFR-pY1069 | biotin-a-a-L-Q-R-pY-S-S-D-P-T-G-amide | |
| EGFR-pY1092 | biotin-a-a-V-P-E-pY-I-N-Q-S-V-P-amide | |
| EGFR-pY1110 | biotin-a-a-N-P-V-pY-H-N-Q-P-L-N-amide | |
| EGFR-pY1125 | biotin-a-a-D-P-H-pY-Q-D-P-H-S-T-amide | |
| EGFR-pY1138 | biotin-a-a-N-P-E-pY-L-N-T-V-Q-P-amide | |
| EGFR-pY1172 | biotin-a-a-N-P-D-pY-Q-Q-D-F-F-P-amide | |
| EGFR-pY1197 | biotin-a-a-N-A-E-pY-L-R-V-A-P-Q-amide | |
| | | |
| *Selected ErbB4 pTyr sites* | | |
| ErbB4-pY1035 | biotin-a-a-P-P-I-pY-T-S-R-A-R-I-amide | |
| ErbB4-pY1066 | biotin-a-a-Q-P-V-pY-R-D-G-G-P-A-amide | |
| ErbB4-pY1208 | biotin-a-a-E-P-L-pY-L-N-T-F-A-N-amide | |
| ErbB4-pY1221 | biotin-a-a-K-A-E-pY-L-K-N-N-I-L-amide | |
| ErbB4-pY1301 | biotin-a-a-P-P-P-pY-R-H-R-N-T-V-amide | |

Fig. 3

Notes to peptide sequences:

"a": 6-aminohexanoic acid

"amide": amidated C-terminus (-CONH$_2$)

"pY": phosphotyrosine

| Position | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Wild type | R | K | A | R | S | E | T | T | A | S | L | S | K | H | K |
| Variant-1 | R | K | A | R | S | E | T | F | E | S | L | S | K | H | R |
| Variant-2 | R | K | A | R | S | E | R | S | D | V | L | S | K | H | K |
| Variant-3 | R | K | A | R | S | E | S | I | A | S | L | S | K | H | L |
| Variant-4 | R | K | A | R | S | E | T | T | S | V | L | S | K | H | L |
| Variant-5 | R | K | A | R | S | E | T | I | S | S | L | S | K | H | L |
| Variant-6 | R | K | A | R | S | E | T | T | A | A | L | S | K | H | I |
| Variant-7 | R | I | A | R | S | E | S | T | A | V | L | S | K | H | K |
| Variant-8 | R | K | A | R | S | E | T | I | D | S | L | S | K | H | L |
| Variant-9 | R | K | A | R | S | E | T | T | A | V | L | S | K | H | K |
| Variant-10 | R | K | A | R | S | P | R | T | V | V | L | S | K | H | K |
| Variant-11 | R | K | A | R | S | E | S | T | A | A | L | S | K | H | L |
| Variant-12 | R | E | A | R | S | E | T | V | A | A | L | S | K | H | I |
| Variant-13 | R | K | A | R | S | E | T | T | A | S | L | S | K | H | L |
| Variant-14 | R | K | A | R | S | E | T | E | A | A | L | S | K | H | K |
| Variant-15 | R | Q | A | R | S | E | T | F | S | A | L | S | K | H | L |
| Variant-16 | R | E | A | R | S | D | N | F | G | V | L | S | K | H | K |
| Variant-17 | R | Q | A | R | S | E | T | S | N | A | L | S | K | H | L |
| Variant-18 | R | T | A | R | S | E | S | V | A | V | L | S | K | H | L |
| Variant-19 | R | K | A | R | S | E | S | I | G | V | L | S | K | H | L |
| Variant-20 | R | E | A | R | S | E | S | R | A | A | L | S | K | H | L |
| Variant-21 | R | K | A | R | S | E | T | I | A | V | L | S | K | H | I |
| Variant-22 | P | R | A | R | R | V | Y | P | P | L | L | S | K | P | S |
| Variant-23 | R | K | A | R | S | E | T | I | A | A | L | S | V | H | L |
| Variant-24 | R | S | A | R | S | E | T | I | A | A | L | S | K | H | L |
| Variant-25 | R | K | A | R | S | E | S | I | A | V | L | S | K | H | I |
| Variant-26 | R | E | A | R | S | E | S | S | A | A | L | S | K | H | L |
| Variant-27 | R | K | A | R | S | E | T | I | A | S | L | S | K | H | L |
| Variant-28 | R | K | A | R | S | A | S | I | A | A | L | S | K | H | L |
| Variant-29 | R | K | A | R | S | E | T | V | A | S | L | S | K | H | L |
| Variant-30 | R | K | A | R | S | K | T | V | A | S | L | S | K | H | L |
| Variant-31 | R | K | A | R | R | E | S | V | E | V | L | S | K | H | R |
| Variant-32 | R | E | A | R | S | E | S | I | A | S | L | S | K | H | L |
| Variant-33 | R | I | A | R | S | E | S | I | A | S | L | S | K | H | L |
| Variant-34 | R | K | A | R | S | E | T | A | A | S | L | S | K | H | L |
| Variant-35 | R | K | A | R | S | G | T | T | A | S | L | S | K | H | L |
| Variant-36 | R | K | A | R | S | E | T | I | A | S | L | S | I | H | L |
| Variant-37 | R | K | A | R | S | E | T | V | A | L | S | K | H | L | L |
| Variant-38 | R | D | A | R | S | E | T | V | A | S | L | S | T | H | L |
| Variant-39 | R | K | A | R | S | E | T | I | A | V | L | S | K | H | L |
| Variant-40 | R | K | A | R | S | E | S | S | D | A | L | S | K | H | I |
| Variant-41 | R | R | A | R | S | E | S | R | L | S | L | S | K | H | L |
| Variant-42 | R | E | A | R | S | E | T | F | D | A | L | S | K | H | V |
| Variant-43 | R | K | A | R | S | E | S | E | A | A | L | S | K | H | K |
| Variant-44 | R | K | A | R | S | E | S | R | A | S | L | S | K | H | L |
| Variant-45 | R | E | A | R | S | E | S | R | A | S | L | S | K | H | L |
| Variant-46 | R | K | A | R | S | E | T | Y | D | S | L | S | K | H | R |
| Variant-47 | R | K | A | R | S | E | T | S | D | A | L | S | K | H | L |
| Variant-48 | R | K | A | R | S | E | S | I | A | A | L | S | N | H | L |
| Variant-49 | R | R | A | R | S | Q | S | I | A | V | L | S | K | H | I |
| Variant-50 | R | K | A | R | S | E | T | I | A | A | L | S | K | H | L |
| Variant-51 | R | K | A | R | S | E | N | V | G | V | L | S | K | H | K |
| Variant-52 | R | K | A | R | S | E | S | T | A | A | L | S | K | H | K |
| Variant-53 | R | K | A | R | S | E | T | A | A | V | L | S | K | H | L |
| Variant-54 | R | K | A | R | S | E | T | Y | A | S | L | S | K | H | L |
| Variant-55 | R | L | A | R | S | D | S | N | G | V | L | S | K | H | K |
| Variant-56 | R | K | A | R | S | E | R | T | A | V | L | S | K | H | K |
| Variant-57 | R | K | A | R | S | V | N | N | A | V | L | S | K | H | K |
| Variant-58 | R | K | A | R | S | K | N | S | G | V | L | S | K | H | R |
| Variant-59 | R | K | A | R | S | E | S | T | A | V | L | S | K | H | K |
| Variant-60 | R | K | A | R | S | E | S | I | A | A | L | S | K | H | L |
| Variant-61 | R | K | A | R | S | V | R | S | G | I | L | S | K | H | K |
| Variant-62 | R | K | A | R | S | K | T | T | A | A | L | S | K | H | K |
| Variant-63 | R | K | A | R | S | E | T | H | A | A | L | S | K | H | L |

Fig. 4

| Position | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| | P | D E I L Q R S T | | | R | A D G K P Q V | N R S Y | A E F H I N P R S V Y | D E G L N P S V | A I L V | | | I N T V | P | I L R S V |

Fig. 5

| pTyr (or Tyr) peptide | Sequence | Notes |
|---|---|---|
| VEGFR1-pY1213 | fluorescein-G-G-D-V-R-pY-V-N-A-A-K-F-amide | Modified from the Wt sequence: DVRpYVNAFKF |
| HaPyV MidT-pY324 | fluorescein-G-G-E-P-Q-pY-R-E-I-P-I-Y-L-amide | hamster polyomavirus middle-T antigen |
| SIG11-pY668 | fluorescein-T-T-E-pY-S-E-I-K-I-H-T-amide | |
| TRAF7-pY275 | fluorescein-G-G-Q-D-T-pY-E-T-H-L-E-T-amide | Not a known physiological phosphorylation site |
| RSKL-pY423 | fluorescein-G-G-Y-Q-H-pY-D-L-D-L-K-D-amide | |
| EGFR-pY978 | fluorescein-G-G-P-Q-R-pY-L-V-I-Q-G-D-amide | |
| EGFR-pY1110 | fluorescein-G-G-N-P-V-pY-H-N-Q-P-L-N-amide | |
| ShcA-pY239 | fluorescein-G-G-D-H-Q-pY-Y-N-D-F-P-G-amide | |
| ShcA-pY317 | fluorescein-G-G-D-P-S-pY-V-N-V-Q-N-L-amide | |
| GGpYGG | fluorescein-G-G-pY-G-G-amide | Designed peptide |
| GGYGG | fluorescein-G-G- Y-G-G-amide | Designed peptide, non-phosphorylated |

Notes to peptide sequences:

"amide": amidated C-terminus (-CONH$_2$)

"pY": phosphotyrosine

| Substitutions → pTyr peptide ↓ | none (wild-type) | T8V | S10V | ΔT8 S10A K15L | S10A | K15L | S10V K15L | K2E T8V S10A K15L | T7S S10A K15L | S10A K15L | T8V S10A K15I | T8V K15L | T8V S10A K15I | T8V S10A K15E | T8V S10A K15L |
|---|---|---|---|---|---|---|---|---|---|---|---|---|---|---|---|
| VEGFR1-pY1213mod | 32 | 24 | 9 | 5.8 | 5.8 | 2.8 | 1.6 | 0.58 | 0.64 | 0.4 | 0.41 | 0.44 | 0.18 | 0.058 |
| EGFR-pY978 | 9.4 | 2.4 | 5.5 | 0.92 | 1.1 | 0.67 | 0.43 | 0.17 | 0.21 | 0.13 | 0.13 | 0.12 | 0.032 | 0.0085 |
| EGFR-pY1110 | 26 | 41 | 34 | 15 | 13 | 5.8 | 4.4 | 3.8 | 1.6 | 2 | 1.4 | 1.7 | 0.7 | 0.34 |
| MidT-pY324 | 0.49 | 0.37 | 0.36 | 0.26 | 0.12 | 0.42 | 0.094 | 0.28 | 0.049 | 0.11 | 0.098 | 0.14 | 0.043 | 0.011 |
| SIG11-pY668 | 0.43 | 1.2 | 0.66 | 0.55 | 0.048 | 0.45 | 0.32 | 0.9 | 0.071 | 0.12 | 0.19 | 0.15 | 0.12 | 0.026 |
| TRAF7-pY275mod | 8 | 5.8 | 4.5 | 2.7 | 1.3 | 2.2 | 2.1 | 0.99 | 0.3 | 0.48 | 0.45 | 0.45 | 0.33 | 0.06 |
| RSKL-pY423 | 12 | 14 | 6.5 | 6.1 | 2.5 | 3.3 | 1.5 | 2.5 | 1.5 | 1.6 | 0.88 | 0.53 | 0.19 | 0.077 |

(b)

| Substitutions → pTyr peptide ↓ | none (wild-type) | T8V | S10V | ΔT8 S10A K15L | S10A | K15L | S10V K15L | K2E T8V S10A K15L | T7S S10A K15L | S10A K15L | T8V S10A K15I | T8V K15L | T8V S10A K15I | T8V S10A K15E | T8V S10A K15L |
|---|---|---|---|---|---|---|---|---|---|---|---|---|---|---|---|
| VEGFR1-pY1213mod | 1.0 | 1.3 | 3.6 | 5.5 | 5.5 | 11.4 | 20.0 | 55.2 | 50.0 | 80.0 | 78.0 | 72.7 | 177.8 | 551.7 |
| EGFR-pY978 | 1.0 | 3.9 | 1.7 | 10.2 | 8.5 | 14.0 | 21.9 | 55.3 | 44.8 | 72.3 | 72.3 | 78.3 | 293.8 | 1105.9 |
| EGFR-pY1110 | 1.0 | 0.6 | 0.8 | 1.7 | 2.0 | 4.5 | 5.9 | 6.8 | 16.3 | 13.0 | 18.6 | 15.3 | 37.1 | 76.5 |
| MidT-pY324 | 1.0 | 1.3 | 1.4 | 1.9 | 4.1 | 1.2 | 5.2 | 1.8 | 10.0 | 4.5 | 5.0 | 3.5 | 11.4 | 44.5 |
| SIG11-pY668 | 1.0 | 0.4 | 0.7 | 0.8 | 9.0 | 1.0 | 1.3 | 0.5 | 6.1 | 3.6 | 2.3 | 2.9 | 3.6 | 16.5 |
| TRAF7-pY275mod | 1.0 | 1.0 | 1.3 | 2.2 | 4.6 | 2.7 | 2.9 | 6.1 | 20.0 | 12.5 | 13.3 | 13.3 | 18.2 | 100.0 |
| RSKL-pY423 | 1.0 | 0.9 | 1.8 | 2.0 | 4.8 | 3.6 | 8.0 | 4.8 | 8.0 | 7.5 | 13.6 | 22.6 | 63.2 | 155.8 |
| Average | 1.0 | 1.4 | 1.6 | 3.5 | 5.5 | 5.5 | 9.1 | 18.5 | 22.2 | 27.6 | 29.0 | 29.8 | 86.4 | 293.0 |

Affinity enhancement →

| Substitutions | none (wild-type) | K15L | T8V C10A | T8V C10A K15L |
|---|---|---|---|---|
| pTyr peptide | | | | |
| VEGFR1-pY1213mod | 6.5 | 1.7 | 1.8 | 0.023 |
| EGFR-pY978 | 3.7 | 0.82 | 0.39 | 0.0077 |
| EGFR-pY1110 | 6.9 | 1.7 | 4.5 | 0.076 |
| MidT-pY324 | 0.13 | 0.051 | 0.027 | 0.0038 |
| RSKL-pY423 | 3.9 | 1.6 | 0.9 | 0.013 |
| ShcA-pY239 | 0.7 | 0.2 | 0.1 | 0.0038 |
| ShcA-pY317 | 2.2 | 0.49 | 0.39 | 0.0075 |

(b)

| Substitutions | none (wild-type) | K15L | T8V C10A | T8V C10A K15L |
|---|---|---|---|---|
| pTyr peptide | | | | |
| VEGFR1-pY1213mod | 1.0 | 3.8 | 3.6 | 282.6 |
| EGFR-pY978 | 1.0 | 4.5 | 9.5 | 480.5 |
| EGFR-pY1110 | 1.0 | 4.1 | 1.5 | 90.8 |
| MidT-pY324 | 1.0 | 2.5 | 4.8 | 34.2 |
| RSKL-pY423 | 1.0 | 2.4 | 4.3 | 300.0 |
| ShcA-pY239 | 1.0 | 3.5 | 7.0 | 184.2 |
| ShcA-pY317 | 1.0 | 4.5 | 5.6 | 293.3 |
| Average | 1.0 | 3.6 | 5.2 | 238.0 |

Fig. 9

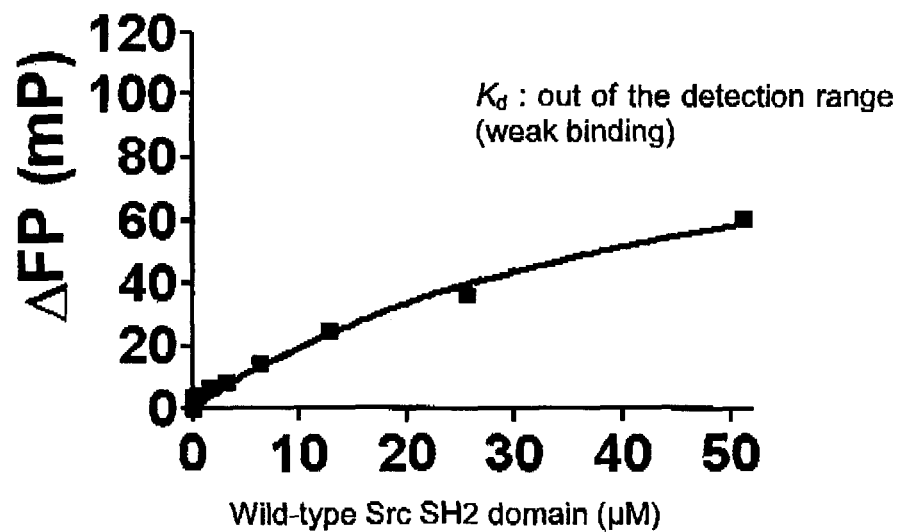
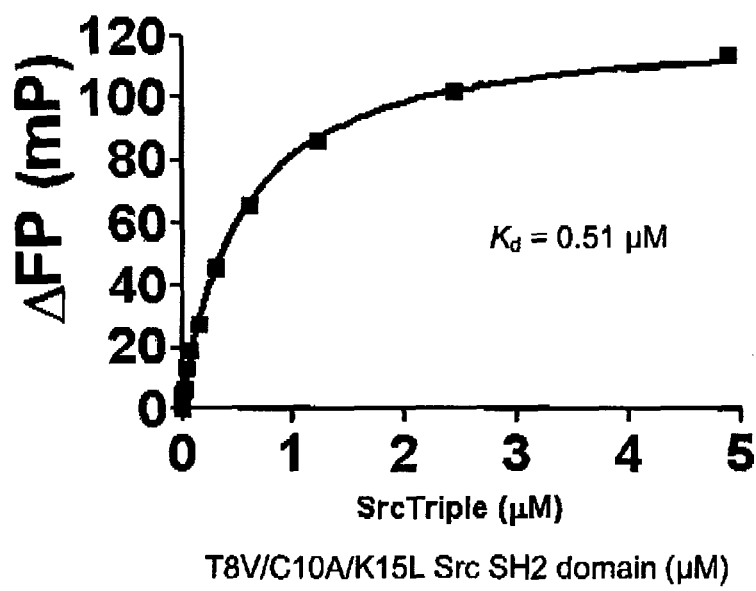
Fig. 10

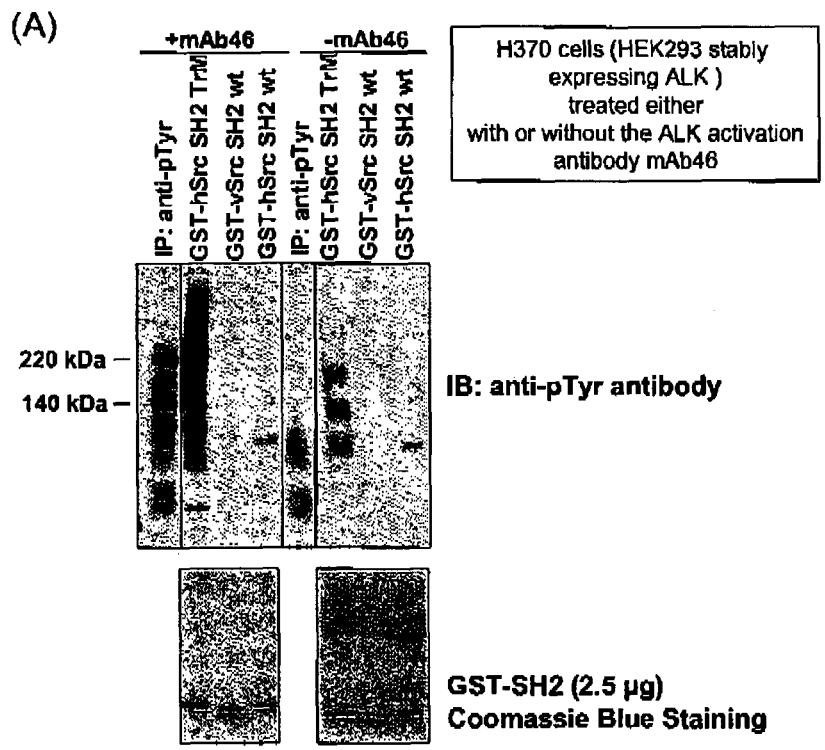
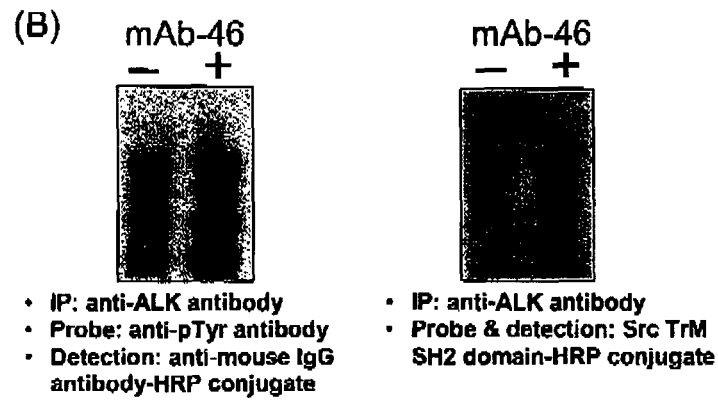
Fig. 15

SH2 DOMAIN VARIANTS

CROSS REFERENCE TO RELATED APPLICATIONS

This application claims the benefit of U.S. Provisional Application No. 61/616,167, filed Mar. 27, 2012, the contents of which are hereby incorporated by reference into the present disclosure in their entirety.

REFERENCE TO A "SEQUENCE LISTING," A TABLE, OR A COMPUTER PROGRAM LISTING APPENDIX SUBMITTED ON A COMPACT DISK

A paper copy of the Sequence Listing and a Sequence Listing in computer readable form in .txt format titled "118494_117SequenceListing.txt", which was submitted online on Sep. 26, 2014, and is 16 KB in size are hereby incorporated by reference. Applicants assert that the paper copy of the Sequence Listing is identical to the Sequence Listing in computer readable form.

FIELD OF THE INVENTION

The present invention relates generally to protein tyrosine kinase signalling, particularly, the present invention relates to polypeptides with enhanced binding affinity to phosphotyrosine-containing peptides or proteins, to methods of using such polypeptides in treating protein tyrosine kinase-associated disorders such as immunologic and oncologic disorders, to methods of using such polypeptides for diagnosing protein tyrosine kinase-associated disorders, to methods of using such polypeptides to detect, track or monitor tyrosine phosphorylation events in cells, to methods of using such polypeptides to enrich or purify phosphotyrosine-containing peptides or proteins, and to pharmaceutical compositions including such polypeptides.

BACKGROUND OF THE INVENTION

Protein tyrosine kinases (PTKs) and their substrates play a critical role in numerous cellular processes such as proliferation, differentiation, motility, and apoptosis. Aberrant kinase activation and the accompanying changes in the phosphotyrosine (designated also as pTyr or pY) signaling network are hallmarks of numerous cancers. A primary mechanism used by the cell to interpret pTyr-mediated signals relies on modular protein domains that bind specifically to tyrosine-phosphorylated proteins. The Src homology 2 (SH2) domain is the most prevalent of these modular domains, and plays a central role in PTK signaling pathways. Different pTyr sites recruit different SH2 domain-containing proteins, which in turn, activate different signaling pathways.

PTKs comprise, inter alia, receptor tyrosine kinases, including members of the epidermal growth factor kinase family. Enhanced activities of PTKs have been implicated in a variety of malignant and non-malignant proliferative diseases. In addition, PTKs are known to play a role in the regulation of cells of the immune system.

PTKs are important drug targets for cancer treatment. Current anti-cancer drugs are largely based on small-molecule kinase inhibitors or humanized antibodies. These drugs often display a broad specificity to a group of related kinases, and patients eventually develop resistance to the drugs after being on the treatment for a year or so.

An alternative idea of inhibiting PTK signaling is blockage of downstream signaling by masking phosphotyrosine of a PTK substrate. Although phosphotyrosine-specific antibodies have high affinity to pTyr-containing polypeptides, they cannot be used inside of cells.

The pTyr-specific antibody (U.S. Pat. No. 6,824,989) is widely used to detect pTyr contained in biological specimen. However, an antibody cannot be used inside of a living cell. An IgG antibody molecule is heterotetrameric protein with the total molecular weight of ~150 kDa that is secreted to the extracellular space by B cells in the immune system. An antibody contains disulfide bonds, works outside of a cell in the immune system, and is not designed to function in cytoplasm or to penetrate the cell plasma membrane. Therefore, the pTyr-specific antibody cannot be used as an in vivo agent for interfering with intracellular signaling events involving protein tyrosine phosphorylation inside of living cells.

SH2 domain containing proteins work downstream of PTK signalling and are points of signal integration. An SH2 domain contains ~100 amino acid and is approximately 15 times smaller than an antibody molecule. Isolated SH2 domains, when delivered or expressed in cells, can compete with endogenous signaling proteins that bind to pTyr sites. However, natural SH2 domains are designed to mediate transient interaction with their cognate binding sites to assure dynamic cellular signaling. In other words, a natural SH2 domain is inherently designed not to block PTK, signaling pathways in vivo. Because of this feature, a natural SH2 domain is not usable as a strong inhibitory reagent.

U.S. Pat. No. 5,786,454 ("U.S. 454") discloses SH2 domains that possess an altered binding site that changes sequence recognition specificity. It has also been reported that modifications of the target-binding site of an SH2 domain, that include deletion, substitution, or introduction of unnatural amino acids, can change sequence recognition specificity of the SH2 domain (Songyang, et al. (1995) J. Biol. Chem., Vol. 270, pp. 26029; Kimber, et al. (2000) Mol. Cell, Vol. 5, pp. 1043; Kaneko, et al. (2010) Sci. Signal., Vol. 3, pp. ra34; Virdee et al. (2010) Chemistry & Biology, Vol. 17, pp. 274). SH2 variants created by this manner exhibit enhanced specificity for their cognate target polypeptides in some cases. However, these SH2 variants generally bind to their cognate target polypeptides with similar affinities as the corresponding natural SH2 domains.

SUMMARY OF THE INVENTION

The present invention relates variant SH2 domains having enhanced binding affinity to phosphotyrosine ("pTyr")-containing peptides or proteins as compared to a parent SH2 domain (including to a wild-type SH2 domain), to methods of using such variant SH2 domains in treating protein tyrosine kinase-associated disorders such as immunologic and oncologic disorders, to methods of using such variant SH2 domains for diagnosing protein tyrosine kinase-associated disorders, to methods of using such variant SH2 domains to track tyrosine phosphorylation events in cells, to the use of such variant SH2 domains as affinity or detection reagents in research, and to pharmaceutical compositions including such variant SH2 domains.

The present invention relates also to a general strategy to enhance binding affinity of an SH2 domain to pTyr-containing peptides. Residue substitutions have been introduced to the pTyr-binding region of an SH2 domain and elucidated favourable substitutions that enhanced binding affinity to pTyr-containing peptides. Different combinations of substitutions show different degrees of impacts in affinity increase, and the generated panel of variant SH2 domains demonstrated an affinity gradient. These affinity-enhanced variants showed tighter binding to a pTyr-containing protein compared to the wild type control SH2 domains in in vitro binding assays and in a mammalian cell line. Therefore, the variant domains function in physiological environment as well as in vitro conditions.

In one embodiment the present invention provides for a variant SH2 domain for binding a phosphotyrosine (pTyr)-containing peptide. In one embodiment, the variant SH2 domain includes a parent SH2 domain having at least one amino acid substitution in a pre-defined region of 15 amino acid positions of the parent SH2 domain that increases the affinity of the variant SH2 domain for the pTyr-containing peptide relative to the parent SH2 domain.

In one embodiment of the variant SH2 domain of the present invention, the pre-defined region of 15 amino acids of the parent SH2 domain corresponds to Arg18 (position 1), Lys19 (position 2), Ala21 (position 3), Arg38 (position 4), Ser40 (position 5), Glu41 (position 6), Thr42 (position 7), Thr43 (position 8), Ala46 (position 9), Ser48 (position 10), Leu49 (position 11), Ser50 (position 12), Lys63 (position 13), His64 (position 14), and Lys66 (position 15) of SEQ ID NO:1 when said parent SH2 domain is aligned with SEQ ID NO:1.

In another embodiment of the variant SH2 domain of the present invention, the at least one substitution includes a substitution to a small or hydrophobic residue at a position in the parent SH2 domain corresponding to position 10.

In another embodiment of the variant SH2 domain of the present invention, the small or hydrophobic residue includes alanine, isoleucine, leucine or valine.

In another embodiment of the variant SH2 domain of the present invention, the at least one substitution includes substitution to a hydrophobic residue at a position in the parent SH2 domain corresponding to position 15.

In another embodiment of the variant SH2 domain of the present invention, the hydrophobic residue includes isoleucine, leucine or valine.

In another embodiment of the variant SH2 domain of the present invention, the at least one substitution includes substitutions at positions in the parent SH2 domain corresponding to positions 10 and 15.

In another embodiment of the variant SH2 domain of the present invention, the at least one substitution includes substitutions at positions in the parent SH2 domain corresponding to positions 8 and 15.

In another embodiment of the variant SH2 domain of the present invention, the at least one substitution includes substitutions at positions in the parent SH2 domain corresponding to positions 8, 10 and 15.

In another embodiment of the variant SH2 domain of the present invention, the substitution corresponding to position 8 comprises a substitution to a phenylalanine, an isoleucine, a proline, or a valine.

In another embodiment of the variant SH2 domain of the present invention, the variant SH2 domain includes an arginine residue in position 4, a leucine residue in position 11 and a serine residue position 12.

In another embodiment of the variant SH2 domain of the present invention, the variant SH2 domain includes an amino acid sequence selected from: SEQ ID NOs:5-17, 19-22.

In another embodiment of the variant SH2 domain of the present invention, the parent SH2 domain is eukaryotic.

The present invention, in one embodiment, also provides for an isolated DNA sequence encoding the variant SH2 domains according to any of the above embodiments.

The present invention, in one embodiment, also provides for a vector comprising the DNA sequence of the previous embodiment.

In one embodiment, the present invention provides for a use of the variant SH2 domains of the present invention for the treatment of a pTyr-containing peptide associated disorder.

In another embodiment, the present invention provides for a use of the variant SH2 domains of the present invention for inhibiting or preventing the effects of a tyrosine kinase in a cell.

In another embodiment, the present invention provides for a method for preventing or inhibiting the effects of a tyrosine kinase in a cell, characterized in that the method includes delivering or introducing a variant SH2 domain of the above embodiments into the cell.

In one aspect of the present invention, the variant SH2 domain is provided within a carrier that allows transportation across the cell.

In another aspect of the present invention, the variant SH2 domain is provided as a fused product to a cell membrane penetrating molecule.

The present invention, in another embodiment, provides also for the use of the variant SH2 domain of the above embodiments for assessing the presence of pTyr-containing peptides in a sample.

In one embodiment, the present invention provides for method of assessing the presence of pTyr-containing peptides in a sample, the method including (a) contacting said sample to a variant SH2 domain of the present invention, such that a pTyr-containing peptide/variant SH2 domain complex is formed if the pTyr-containing peptides are present in the sample; and (b) detecting the formation of the complex, thereby detecting the presence of the pTyr-containing peptides in the sample.

The present invention, in another embodiment, provides also for the use of the variant SH2 domain of the present invention for the study of the pTyr-containing peptide signalling pathway and/or for isolating pTyr-containing peptides.

In one embodiment, the present invention relates to a method for isolating pTyr-containing peptides from a sample, characterized in that the method includes: (a) contacting said sample to a variant SH2 domain of the present invention such that a pTyr-containing peptide/variant SH2 domain complex is formed if the pTyr-containing peptides are present in the sample; and (b) releasing the pTyr-containing peptides from the complex, thereby isolating the pTyr-containing peptides from the sample.

In one aspect of the previous method, the method further includes determining the concentration of the pTyr-containing peptides in the sample by measuring the amount of pTyr-containing peptides released.

In another embodiment, the present invention provides for a method of determining the concentration of pTyr-containing peptides in a sample, the method including: (a) immobilizing a variant SH2 domain of the present invention on a resin, (b) passing the sample through the resin with the bound variant SH2 domain, (c) releasing any pTyr-containing peptide bound to the resin by adding a solvent that removes the ability for the variant SH2 domain to bind to the pTyr-containing peptide thereby creating elution fractions, and (d) determining the concentration of the pTyr-containing peptides present in the elution fractions.

In aspects of the present invention, the concentration of pTyr-containing peptides is determined through high performance liquid chromatography (HPLC).

In aspects of the present invention the variant SH2 domain is bound to an affinity column or onto a lateral flow strip.

The present invention provides, in another embodiment, a use of the variant SH2 domain of the present invention for the binding or detection of pTyr residue(s) in a peptide or protein in vitro or in vivo.

The present invention, in another embodiment, provides for a method of manufacturing a variant SH2 domain having enhanced binding affinity for a pTyr-containing peptide relative to a parent SH2 domain, characterized in that the method includes substituting at least one amino acid residue in a pre-defined region of 15 amino acid positions of the parent SH2 domain, the pre-defined region of 15 amino acids of the parent SH2 domain corresponding to Arg18 (position 1), Lys19 (position 2), Ala21 (position 3), Arg38 (position 4), Ser40 (position 5), Glu41 (position 6), Thr42 (position 7), Thr43 (position 8), Ala46 (position 9), Ser48 (position 10), Leu49 (position 11), Ser50 (position 12), Lys63 (position 13), His64 (position 14), and Lys66 (position 15) of SEQ ID NO:1 when said parent SH2 domain is aligned with SEQ ID NO:1.

In one embodiment, the present invention provides for a polypeptide comprising multiple SH2 domains, at least one of the multiple SH2 domains in the polypeptide being a variant SH2 domain of the present invention.

These and other aspects of the invention will become apparent from the detailed description by reference to the following Figures.

BRIEF DESCRIPTION OF THE FIGURES

The present invention will become more fully understood from the detailed description given herein and from the accompanying drawings, which are given by way of illustration only and do not limit the intended scope of the invention.

FIG. 1(A) illustrates the position of the 15 residue positions surrounding pTyr and a sequence alignment utilized for defining the positions.

FIG. 2 (a) shows the position of the 15 residue positions surrounding pTyr and a sequence alignment utilized for defining the positions. The 15 positions are defined, according to one embodiment, on the Fyn SH2 domain (residues shaded black on FIG. 2a). The sequence alignment (FIG. 2a) contains the human Fyn SH2 domain (starting from residue W149), the human Src SH2 domain (starting from residue W151) and the human Grb2 SH2 domain (starting from residue W60). The 15 positions on an SH2 domain can be defined from a sequence alignment that includes the human Fyn SH2 domain (FIG. 2a).

FIG. 2 (b) illustrates one embodiment for determining the 15 positions when an alignment gap exists in an alignment. According to the embodiment illustrated in FIG. 2(b) arginine at position 4 is defined first, and then residues at position 5, 6, 7, and 8 will be identified as the second, third, fourth, and fifth residues, respectively, C-terminal to the residue at position 4. FIG. 2 (c) illustrates a comparison between the numbering of the 15 positions according to the present invention and the corresponding numbering system defined by Eck et al. (1993, Nature, Vol. 362, pp. 87).

FIG. 3 lists pTyr-containing synthetic peptides used for the phage display screening experiments of the present invention. These peptides are biotinylated at their N-terminus and amidated at their C-terminus.

FIG. 4 is a table showing residues at the 15 positions in 63 variants of the human Fyn SH2 domain, obtained in accordance to one embodiment of the present invention. Residues substituted from the wild type are shaded black.

FIG. 5 is a table showing a list of substituted residues observed in the 63 variants of FIG. 4.

FIG. 6 lists pTyr-containing synthetic peptides used for the fluorescence polarization assay of the present invention. These peptides are fluorescein-labeled at their N-terminus and amidated at their C-terminus.

FIG. 7 shows results of in-solution fluorescence polarization binding assay that determines affinity of interaction between the Fyn SH2 domain and peptides listed in FIG. 5. FIG. 7 (a) shows dissociation constant (Kd) values (in μM unit) of interaction between the peptides and variant Fyn SH2 domains that contain substitutions indicated in the first row. Affinity increase relative to the wild type for each peptide-variant combination is calculated and shown in FIG. 7 (b). The variants are sorted from left to right according to the average affinity increase.

FIG. 8 (a) shows binding of the wild-type Fyn SH2 domain to the fluorescein-GGpYGG peptide (SEQ ID NO: 23). FIG. 8 (b) shows binding of the T8V/S10A/K15L variant Fyn SH2 domain to the fluorescein-GGpYGG peptide (SEQ ID NO: 23). FIG. 8 (c) shows no apparent signal observed between the T8V/S10A/K15L variant SH2 domain and a non-phosphorylated fluorescein-GGYGG peptide (SEQ ID NO: 24).

FIG. 9 are tables illustrating results of in-solution fluorescence polarization binding assay that determines affinity of interaction between the Src SH2 domain and peptides listed in FIG. 5. FIG. 9 (a) is a table showing Kd values (in μM unit) of interaction between pTyr-containing peptides and the wild-type or variant Src SH2 domains. Affinity increase relative to the wild type for each peptide-variant combination is calculated and shown in FIG. 9 (b).

FIG. 10 (a) is a graph showing binding curve and Kd values of the wild-type Src SH2 domain to the fluorescein-GGpYGG peptide (SEQ ID NO: 23). FIG. 10 (b) is a graph showing binding curve and Kd values of the T8V/C10A/K15L variant Src SH2 domain to the fluorescein-GGpYGG peptide (SEQ ID NO: 23).

FIG. 11 (a) is a photograph of a Western, blotting showing that TrM SH2 domains bind to EGFR much tighter than Wt domains. IP: immunoprecipitation, immunoblotting. FIG. 11 (b) shows Erk phosphorylation is significantly reduced in cells that express TrM SH2 domains. Erk is located downstream of the EGFR signaling pathway. FIG. 11 (c) is a graph showing quantification of the band intensity of pErk in FIG. 11 (b), relative to the GFP empty vector control set as 100%.

FIG. 12 (a) is a graph showing inhibitory effect on cell viability relative to the GFP empty vector control. FIG. 12 (b) is a graph showing inhibitory effect of the 8V/10A/15L-substituted SH2 domains to colony formation observed by the soft agar assay, quantified relative to the GFP empty vector control. FIG. 12 (c) are example photos of the colonies quantified in FIG. 12(b). In FIGS. 12(a) and 12(b), black bars represent TrM and white bars represent Wt. The numbers are calculated relative to GFP empty vector control sample (set as 100%).

FIG. 15 Panel A shows a comparison in ability to pull down a tyrosyl phosphorylated protein between GST-SrcSH2 TrM and an anti-pTyr mouse monoclonal antibody (Cell Signaling, #9411) Cell lysate from the H370 cell line, an HEK293 cell line stably expressing human anaplastic lymphoma kinase (ALK), was used here. ALK produces a 220 kDa protein which is then cleaved proteolytically to yield smaller fragments, including one at 140 kDa. ALK is tyrosine phosphorylated upon stimulation with the antibody mAb46 (described in Moog-Lutz C, Degoutin J, Gouzi J Y, Frobert Y, Brunet-de Carvalho N, Bureau J, Créminon C, Vigny M. J Biol Chem. 2005 Jul. 15; 280(28):26039-48. Epub 2005 May 10). The top panel shows Western blot result revealed with the anti-pTyr antibody. IP: immunoprecipitation using anti-pTyr antibody and Protein-G beads. GST-SH2 domain lanes: samples from GST-pulldown experiments. hSrc: human Src. vSrc: Rous sarcoma virus Src. Panel B shows the SrcTrM SH2 domain conjugated with HRP (horseradish peroxidase) can detect phosphorylated ALK protein species on a PVDF membrane.

DETAILED DESCRIPTION OF THE INVENTION

Definitions

Figure 1:
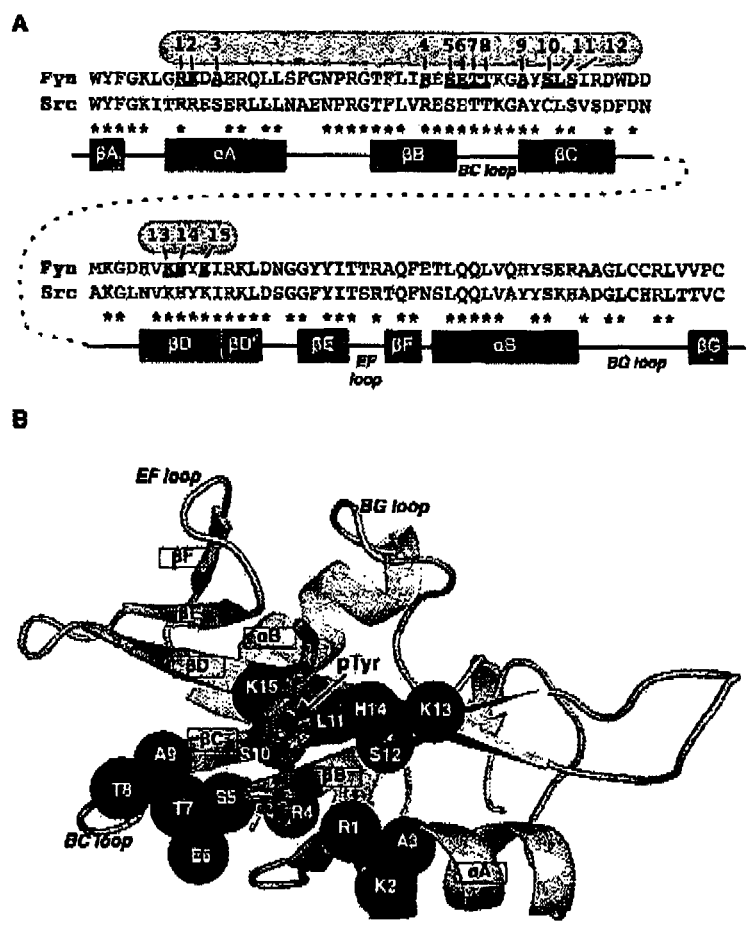
FIG. 1 (B) shows the binding site of pTyr on the human Fyn SH2 domain. The atomic coordinates are derived from the Protein Data Bank ID: 1AOT (Mulhern et al. (1997) Structure, Vol. 5, pp. 1313), which describes the structure of the Fyn SH2 domain and a bound pTyr-containing peptide. In this figure, only the pTyr residue within the bound peptide is shown for clarity, in stick representation. 15 SH2 domain residues surrounding the bound pTyr are shaded in dark gray. The backbone structure of the SH2 domain is shown as ribbon representation. Locations of the 15 residues are displayed with ball representation.

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise.

The following standard one letter and three letter abbreviations for the amino acid residues may be used throughout the specification: A, Ala—alanine; R, Arg—Arginine; N, Asn—Asparagine; D, Asp—Aspartic acid; C, Cys—Cysteine; Q, Gln—Glutamine; E, Glu—Glutamic acid; G, Gly—Glycine; H, His—Histidine; I, Ile—Isoleucine; L, Leu—Leucine; K, Lys—Lysine; M, Met—Methionine; F, Phe—Phenylalanine; P, Pro—Proline; S, Ser—Serine; T, Thr—Threonine; W, Trp—Tryptophan; Y, Tyr—Tyrosine; and V, Val—Valine.

"pTyr-containing polypeptide" refers to a molecule that comprises a pTyr-containing peptide fragment.

The term "parent SH2 domain" includes any eukaryotic SH2 domain or a polypeptide having at least about 50% sequence identity to an SH2 domain derived from a human protein that contains an SH2 domain. One hundred and eleven (111) human proteins that contain an SH2 domain are identified in Liu et al. (2011) Science Signaling, Vol. 4, pp. ra83 (see Table 1). Sequence identity can be determined by comparing a position in each sequence of about 100 amino acid residues which may be aligned for purposes of comparison. The sequence identity between sequences is a function of the number of matching positions shared by the sequences. As such, the term "parent SH2" domain includes also artificially made sequences and viral SH2 domains. For example, one can generate or design artificial SH2 domain sequences as parent SH2 domains based on one or more mammalian SH2 domain sequences, which would represent a quintessential SH2 domain sequence, but would not be identical to any mammalian SH2. Another example may be v-Src, encoded by the Rous Sarcoma virus, which is a viral homolog of human Src with little sequence deviation.

The term "fragment" refers to any subject peptide having an amino acid residue sequence shorter than that of a peptide whose amino acid residue sequence is shown herein.

The term "isolated peptide" or "isolated DNA" may be defined as a peptide or DNA molecule, as the case may be, which is substantially separated from other cellular components which may naturally accompany the peptide and DNA. The term includes, without limitation, recombinant or cloned DNA isolates and chemically synthesized analogs or analogs biologically synthesized by heterologous systems.

The term "ligand" means a molecule that binds another molecule or target.

The term "peptide" or "polypeptide" as used herein is defined as a chain of amino acid residues, usually having a defined sequence. As used herein the term "peptide" is mutually inclusive of the terms "polypeptides", "peptides" and "proteins".

The terms "variant SH2 domain", "SH2 Variant", "SH2 monobody" are used indistinguishably to refer to a parent SH2 domain that incorporates the substitutions for affinity enhancement of the present invention. The present invention applies to a variant SH2 domain of a parent SH2 domain, as well as to a variant of a fragment of a parent SH2 domain that contains a region between position 1 and position 15 (as this positions are defined below). In aspects of the present invention, the use of a variant SH2 domain for clinical or diagnostic use in a human, is preferably designed from a human SH2 domain as a parent SH2 domain, in order to minimize the possibility of immune response that may be caused by supplementation of the variant SH2 domain to the body.

The priority document and all documents referred to in this application are incorporated herein by reference in their entirety.

Overview of the Invention

The present invention relates in general to variant of SH2 domains and methods of obtaining said variants. The variant SH2(s) of the present invention may be used to isolate pTyr-containing molecules, such as peptides, including polypeptides and proteins, measuring the concentration of pTyr-containing molecules in a sample, or merely detecting the presence of pTyr-containing molecules in a sample. The variant SH2 domains of the present invention may also be used in other applications such as for therapeutic, diagnosis or as reagents for research purposes.

SH2 Domain Variant

Applicants have invented SH2 variant(s) and a strategy to enhance binding affinity of an SH2 domain to a pTyr-containing polypeptide. The strategy of the present invention may include making single or multiple amino acid residue substitutions on a parent SH2 domain protein sequence.

The substitutions are applied to pre-defined 15 amino acid positions on an SH2 domain. An SH2 domain may be used as a standard. For example, as a standard, these positions may be defined on the amino acid sequence of the human Fyn SH2 domain as illustrated in FIG. 1 and FIG. 2 (a). However, a person of ordinary skill in the art understands that other SH2 domains may be used as standards for example the Src SH2 domain, the GRB2 SH2 domain and so forth. With reference to FIG. 1, the 15 positions correspond to 15 amino acid residues surrounding pTyr in the atomic structure. These positions may be consecutively numbered from position 1 to position 15 (FIG. 1 A and FIG. 2 (a)). Corresponding 15 positions on other SH2 domains may be defined by protein sequence alignment. Positions 1, 2, 3, 4, 9, 10, 11, 12, 13, 14, and 15 on a parent SI-12 domain sequence may be directly identified from an alignment, by referring to the Fyn SH2 domain as a standard (FIG. 2(a)). Positions 5, 6, 7 and 8 may also be directly identified from the alignment. In one embodiment, positions 5, 6, 7, and 8 may be defined counting from position 4 (FIG. 2(b)). This embodiment may be used, for example, to avoid potential sequence gap problems in the BC loop region shown in FIG. 1 A. Positions 5, 6, 7, and 8 correspond to four continuous residues, and a residue at position 5 is located two residues C-terminal to the residue at position 4. These positions correspond to an SH2 domain sequence nomenclature system defined by Eck et al. (see FIG. 2 (c)).

FIG. 5 lists amino acid residues within the 15 positions from which one or multiple residues of substitutions are chosen for creating a variant SH2 domain. In one embodiment, the variant SH2(s) of the present invention may include one residue substitution. For affinity enhancement, in one embodiment, it may be favourable to substitute a residue at positions 10 to a small or hydrophobic residue, including alanine, isoleucine, leucine, or valine. It may also be favourable to substitute a residue at position 15 to a hydrophobic residue, including isoleucine, leucine, or valine.

For further affinity enhancement, in another embodiment, it may be favourable to employ two substitutions in a variant SH2 domain. For example, a substitution at positions 1 and 2, or 1 and 5, or 1 and 6 or 1 and 7 and any possible combination between any two positions that would result in a SH2 variant with enhanced pTyr binding. In one embodiment, it may be favourable to include substitutions at positions 10 and 15. It may also be especially favourable to simultaneously substitute residues at positions 8 and 15 to hydrophobic residues. These substitutions include a residue at position 8 to phenylalanine, isoleucine, proline, or valine, in combination with a residue at position 15 to isoleucine, leucine, or valine.

For further affinity enhancement, in another embodiment, it may be favourable to employ three substitutions in a variant SH2 domain. For example, a substitution at positions 1, 2 and 5 or 1, 2 and 6, or 1, 2 and 7 or any possible combination between any three positions that would result in a SH2 variant with enhanced pTyr binding. In one embodiment, it may be especially desired to simultaneously employ the three favourable substitutions at positions 8, 10, and 15 in a variant domain. More than 3 substitutions within the 15 amino acid residues are also covered by the present disclosure.

In one embodiment of the present invention a protein molecule may be designed to contain multiple SH2 domains, in which at least one of them is a variant SH2 domain. For example, a protein that comprises multiple SH2 domains, each of which targets different pTyr-containing binding site, may be designed and created. Use of a variant SH2 domain in a multi-SH2 domain construct further increases binding affinity, toward a target protein that contains multiple pTyr-containing binding sites. SH2 domains are connected by a flexible linker material, preferably a polypeptide that contains glycine. Variation of the linker length and composition further changes binding affinity of a multi-SH2 domain protein. A multi-SH2 domain protein may have increased affinity to a multi-pTyr region such as the ITAM motif of a single protein. A multi-SH2 domain protein may also serve to bridge multiple proteins through pTyr sites in target proteins. Inclusion of a variant SH2 domain to a multi-SH2 domain protein may result in increased tightness of binding or bridging.

The affinity of the SH2 variant(s) of the present invention to a pTyr-containing polypeptide is fine-tunable by optimizing a combination of substitutions applied to a parent SH2 domain. In addition, the affinity enhancement substitutions may be combined with other substitutions that modify sequence recognition specificity. Therefore, a variant SH2 domain has an advantage of tunable variability in binding feature to a target pTyr-containing sequence, including variable binding affinity, variable sequence recognition specificity, and modularity to connect multiple domains in tandem. A variant SH2 domain may gain further variability of function by incorporating an unnatural amino acid within a domain sequence. For example, incorporation of a photo-crosslinkable amino acid, p-Trifluoromethyl-diazirinyl-1-phenylalanine, into a natural SH2 domain has been reported, that aids mass spectroscopic detection of direct interaction between the SH2 domain and a target pTyr-containing protein (Hino et al. 2011 J Mol Biol. Vol. 406, pp. 343). Incorporation of a photo-crosslinkable amino acid into the target-binding site of a variant SH2 domain can help permanent blocking of the target pTyr-containing binding site.

The SH2 monobodies of the present invention may be synthesized by any known method in the art of peptide synthesis including solid phase synthesis (Merrifield (1964) J. Am. Chem. Assoc. 65:2149; J. Amer. Chem. Soc. 85:2149 (1963); and Int. J. Peptide Protein Res. 35:161-214 (1990)) or synthesis in homogenous solution (Methods of Organic Chemistry, E. Wansch (Ed.) Vol. 15, pts. I and II, Thieme, Stuttgart (1987) to generate synthetic peptides.

Alternatively, the variant SH2 domains of the invention may be made by the use of recombinant DNA techniques known to one skilled in the art. Nucleic acid sequences which encode for the selected peptides of the invention may be incorporated in a known manner into appropriate expression vectors (i.e. recombinant expression vectors). Possible expression vectors include (but are not limited to) cosmids, plasmids, or modified viruses (e.g. replication defective retroviruses, adenoviruses and adeno associated viruses, lentiviruses; herpes viruses, poxviruses), so long as the vector is compatible with the host cell used. The expression "vector is compatible with the host cell" is defined as contemplating that the expression vector(s) contain a nucleic acid molecule of the invention (hereinafter described) and attendant regulatory sequence(s) selected on the basis of the host cell(s) to be used for expression, said regulatory sequence(s) being operatively linked to the nucleic acid molecule. "Operatively linked" is intended to mean that the nucleic acid is linked to regulatory sequence(s) in a manner which allows expression of the nucleic acid. Suitable regulatory sequences may be derived from a variety of sources, including bacteria), fungal, or viral genes. (For example, see the regulatory sequences described in Goeddel, Gene Expression Technology: Methods in Enzymology 185, Academic Press, San Diego, Calif. (1990)., Selection of appropriate regulatory sequence(s) is dependent on the host cell(s) chosen, and may be readily accomplished by one of ordinary skill in the art. Examples of such regulatory sequences include the following: a transcriptional promoter and enhancer, RNA polymerase binding sequence, or a ribosomal binding sequence (including a translation initiation signal). Depending on the host cell chosen and the expression vector employed, other additional sequences (such as an origin of replication, additional DNA restriction sites, enhancers, and sequences conferring inducibility of transcription) may be incorporated into the expression vector.

It is further contemplated that the invention encompasses vectors which comprise nucleic acids coding for at least one SH2 monobody.

The SH2 monobodies of the present invention may be provided with a cell membrane penetrating peptide, such as a TAT protein transduction domain, or an Arg-rich peptide, or another peptide, or liposomes, or nanoparticles, or any other carrier material that facilitates the delivery of the SH2 monobodies into cells or tissues. TAT-fusions have been shown to cross cell membranes and, in some instances, blood barriers. In this regard, Applicants have confirmed that purified TAT-SH2 domains (labelled with FITC) penetrate cells and have half-lives of 2-3 days in cell culture (see FIG. 13).

The variant SH2 domains of the invention may be labelled with a label to facilitate their detection in a variety of assays as is understood by one of skill in the art. Such labels may include but are not limited to radioactive label, a cytotoxic label and fluorescent label. The SH2 monobodies of the invention may be provided with a carrier such as for example couple to bovine serum albumin (BSA) or keyhole limpet haemocyanin. The peptides may be covalently or non-covalently coupled to a solid carrier such as a microsphere of gold or polystyrene, a slide, chip or to a wall of a microtitre plate. The peptide may be labelled directly or indirectly with a label selected from but not limited to biotin, fluorescein and an enzyme such as horseradish peroxidase. For example, the variant SH2(s) may be preceded by a Biotin N-terminal sequence that may facilitate peptide concentration determination by OD280 (of Tyr or Y) measurement (see FIG. 3).

The present invention also provides pharmaceutical compositions comprising a variant SH2 capable of treating a protein. tyrosine kinase-associated disorder in an amount effective therefor, and a pharmaceutically acceptable carrier, vehicle or diluent. The pharmaceutical composition may be administered to a subject in a biologically compatible form for administration in vivo. The peptides of the invention may be provided within DNA expression vectors as described above that are formulated in a suitable pharmaceutical composition.

By "biologically compatible form suitable for administration in vivo" is meant a form of the substance to be administered in which any toxic effects are outweighed by the therapeutic effects. Administration of a therapeutically active amount of the pharmaceutical compositions of the present invention, or an "effective amount", is defined as an amount effective at dosages and for periods of time, necessary to achieve the desired result. A therapeutically effective amount of a substance may vary according to factors such as the disease state/health, age, sex, and weight of the recipient, and the inherent ability of the particular polypeptide, nucleic acid coding therefor, or recombinant virus to elicit a desired response. Dosage regima may be adjusted to provide the optimum therapeutic response. For example, several divided doses may be administered daily or on at periodic intervals, and/or the dose may be proportionally reduced as indicated by the exigencies of the therapeutic situation. The amount of variant SH2 for administration will depend on the route of administration, time of administration and varied in accordance with individual subject responses.

The variant SH2s may be administered by any suitable means, for example, orally, such as in the form of tablets, capsules, granules or powders; sublingually; buccally; parenterally, such as by subcutaneous, intravenous, intramuscular, intraperitoneal or intrasternal injection or infusion techniques (e. g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present variant SH2 may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

The compositions described herein can be prepared by per se known methods for the preparation of pharmaceutically acceptable compositions which can be administered to subjects, such that an effective quantity of the active substance (i.e. SH2 variant peptide) is combined in a mixture with a pharmaceutically acceptable vehicle. Suitable vehicles are described, for example, in "Handbook of Pharmaceutical Additives" (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456.

Pharmaceutical acceptable carriers are well known to those skilled in the art and include, for example, sterile saline, lactose, sucrose, calcium phosphate, gelatin, dextrin, agar, pectin, peanut oil, olive oil, sesame oil and water. Other carriers may be, for example MHC class II molecules. Soluble MHC class II molecules including monomers, dimers, trimers, tetramers, etc, as well as citrulline peptide/MHC class II complexes can be made by methods disclosed in U.S. Pat. No. 5,869,270 (the disclosure of which is incorporated herein by reference).

Furthermore the pharmaceutical composition according to the invention may comprise one or more stabilizers such as, for example, carbohydrates including sorbitol, mannitol, starch, sucrose, dextrin and glucose, proteins such as albumin or casein, and buffers like alkaline phosphates.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The variant SH2(s) of the present invention may be employed alone or in combination with each other and/or other suitable therapeutic agents useful in the treatment of protein tyrosine kinase-associated disorders such as PTK inhibitors other than those of the present invention, antiinflammatories, antiproliferatives, chemotherapeutic agents, immunosuppressants, anticancer agents and cytotoxic agents.

Exemplary such other therapeutic agents include the following: cyclosporins (e. g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i. e., CD154), fusion proteins constructed from CD40 and gp39 (CD40Ig and CD8gp39), inhibitors, such as nuclear translocation inhibitors, of NF-kappa B function, such as deoxyspergualin (DSG), non-steroidal anti-inflammatory drugs (NSAIDs) such as ibuprofen, steroids such as prednisone or dexamethasone, gold compounds, anti-proliferative agents such as methotrexate, FK506 (tacrolimus, Prograf), mycophenolate mofetil, cytotoxic drugs such as azathiprine and cyclophosphamide, TNF-oc inhibitors such as tenidap, anti-TNF antibodies or soluble TNF receptor such as etanercept (Enbrel), rapamycin (sirolimus or Rapamune), leflunimide (Arava), and cyclooxygenase-2 (COX-2) inhibitors such as celecoxib (Celebrex) and rofecoxib (Vioxx), or derivatives thereof, and the PTK inhibitors.

Therapeutic Uses

The variant SH2 of the present invention inhibit the action of protein tyrosine kinases, especially Src-family kinases such as Lck, Fyn, Lyn, Src, Yes, Hck, Fgr and Blk, and may thus be useful in the treatment, including prevention and therapy, of protein tyrosine kinase-associated disorders such as immunologic and oncologic disorders. The variant SH2 domains of the present invention inhibit also the action of receptor tyrosine kinases including EGFR and may therefore be useful in the treatment of proliferative disorders such as psoriasis and cancer. The ability of these variant SH2 to inhibit EGFR and other receptor kinases may also permit their use as anti-angiogenic agents to treat disorders such as cancer and diabetic retinopathy. "Protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a particularly preferred embodiment of the present invention. Compounds which selectively block T cell activation and proliferation may be preferred. Compounds of the present invention which block the activation of endothelial cell PTK by oxidative stress, thereby limiting surface expression of adhesion molecules that induce neutrophil binding, and which inhibit PTK necessary for neutrophil activation may be useful, for example, in the treatment of ischemia and reperfusion injury.

The present invention thus provides methods for the treatment of protein tyrosine kinase-associated disorders, comprising the step of administering to a subject in need thereof a variant SH2 in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention. In embodiments of the present invention, the variant SH2 may be provided as a fused product to a membrane penetrating peptide such as a TAT protein transduction domain. The variant SH2 may also be provided within a carrier that allows transportation across a cell membrane.

Use of the variant SH2 of the present invention in treating protein tyrosine kinase-associated disorders is exemplified by, but is not limited to, treating a range of disorders such as: transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; chronic obstructive pulmonary disease (COPE)), such as emphysema; inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including cancers where Lck or other Src-family kinases such as Src are activated or overexpressed, such as colon carcinoma and thymoma, and cancers where Src-family kinase activity facilitates tumor growth or survival; glomerulonephritis; serum sickness; uticaria; allergic diseases such as respiratory allergies (asthma, hayfever, allergic rhinitis) or skin allergies; scleracierma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides a method for treating the aforementioned disorders such as atopic dermatitis by administration of any compound capable of inhibiting protein tyrosine kinase.

Src-family kinases other than Lck, such as Hck and Fgr, are important in the Fc gamma receptor responses of monocytes and macrophages. Variant SH2 domains of the present invention inhibit the Fc gamma dependent production of TNF alpha in the monocyte cell line THP-1 that does not express Lck. The ability to inhibit Fc gamma receptor dependent monocyte and macrophage responses results in additional anti-inflammatory activity for the present compounds beyond their effects on T cells. This activity is especially of value, for example, in the treatment of inflammatory diseases such as arthritis or inflammatory bowel disease.

In particular, the present SH2 monobody(ies) may be of value for the treatment of autoimmune glomerulonephritis and other instances of glomerulonephritis induced by deposition of immune complexes in the kidney that trigger Fc gamma receptor responses leading to kidney damage.

In addition, Src family kinases other than Lck, such as Lyn and Src, are important in the Fc epsilon receptor induced degranulation of mast cells and basophils that plays an important role in asthma, allergic rhinitis, and other allergic disease. Fc epsilon receptors are stimulated by IgE-antigen complexes. Variant SH2s of the present invention inhibit the Fc epsilon induced degranulation responses, including in the basophil cell line RBL that does not express Lck. The ability to inhibit Fc epsilon receptor dependent mast cell and basophil responses results in additional anti-inflammatory activity for the present compounds beyond their effect on T cells. In particular, the present compounds are of value for the treatment of asthma, allergic rhinitis, and other instances of allergic disease.

The combined activity of the present variant SH2 towards monocytes, macrophages, T cells, etc. may be of value in the treatment of any of the aforementioned disorders.

By virtue of their ability to inhibit EGFRs, variant SH2 of the present invention may also be used for the treatment of proliferative diseases, including psoriasis and cancer. The HER1 receptor kinase has been shown to be expressed and activated in many solid tumors including non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor efficacy in preclinical and clinical studies. It is therefore expected that inhibitors of the HER1 and HER2 kinases will have efficacy in the treatment of tumors that depend on signaling from either of the two receptors. These compounds may be expected to have efficacy either as single agent or in combination with other chemotherapeutic agents such as placlitaxel (Taxol), doxorubicin hydrochloride (adriamycin), and cisplatin (Platinol). See the following documents and references cited therein: Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J.,"Multinational study of the efficacy and safety of humanized anti-HER2 monoclonal antibody in women who have HER2-overexpressing metastatic breast cancer that has progressed after chemotherapy for metastatic disease", J. of Clin. Oncol. 17 (9), p. 2639-2648 (1999); Baselga, J., Pister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", J. Clin. Oncol. 18 (4), p. 904-914 (2000).

The above other therapeutic agents, which is not exhaustive, when employed in combination with the compounds of the present invention, may be used, for example, in those amounts indicated in the Physicians' Desk Reference (PDR) or as otherwise determined by one of ordinary skill in the art.

Diagnosis

According to another embodiment of the invention, provided is a method for diagnosing a protein tyrosine kinase associated disorder in a subject.

In one embodiment a subject's sample may be contacted with a SH2 variant of the present invention to measure phosphorylated proteins in the sample. An increase in the amount of phosphorylated proteins in the sample relative to the amount of phoshphorylated proteins in a normal control sample, may be indicative of a protein kinase associated disorder.

Tissue samples may include tissue lysates, blood, and other bodily fluids. The tissue samples may be tested for kinase activation by using the SH2 variant of the present invention to detect phosphorylated proteins in the tissue sample. The test may also be done with tissue histology by using fluorescence-labelled SH2 variants to image phosphorylated proteins on tissue slices; ELISA-based, combining SH2 variants with an antibody specific for a target protein to assay its phosphorylation in normal and disease tissues (or cells), and so forth.

Another application is in viva imaging. SH2 variant labelled with an imaging tag used for in vivo imaging of tumours, PET, MRI, etc. Cancer tissues characterized with aberrant kinase activation may display enhanced protein phosphorylation relative to normal tissues, which can be detected and imaged using SH2 variant-based imaging tools.

Another embodiment may include SH2 profiling based on Bruce Mayer's method (U.S. Pat. No. 7,846,746), to compare binding profiles of normal and disease cell lysates. Yet another embodiment may include injecting a radiolabeled and maybe TAT-tagged variant SH2 domain to a cancer patient to detect SH2 accumulation to a tumor site in the patient's body.

To detect the SH2 variant in the samples, the variant SH2 domain of the present invention may preferably be labelled with a probe molecule.

Detection of pTyr-positive cells may be carried out by a probe. The probe may include at least a peptide comprising a SH2 variant and an imaging component. Optionally, this probe may be labelled with a detectable marker which may allow detection of the location of the pTyr-positive cells. The probe of the present invention may allow following movement and development of pTyr-positive cells.

Methods of preparing probes are well known to those of skill in the art (see, e.g. Sambrook et al, Molecular Cloning: A Laboratory Manual (2nd ed.), Vols. 1-3, Cold Spring Harbor Laboratory, (1989) or Current Protocols in Molecular Biology, F. Ausubel et al., ed. Greene Publishing and Wiley-Interscience, New York (1987)), which are hereby incorporated by reference.

The imaging component of the probe may generally comprise a label. Methods of labelling are well known to those of skill in the art. Preferred labels may be those which are suitable for use in in vivo imaging. The SH2 monobody probes may be detectably labelled prior to detection. Alternatively, a detectable label which may bind to the hybridization product may be used. Such detectable labels may include, without limitation, any material having a detectable physical or chemical property and have been well-developed in the field of immunoassays. A label for use in the present invention may be any composition detectable by spectroscopic, photochemical, biochemical, immunochemical, or chemical means.

Labels which may be used in the present invention include biotin-based label, magnetic label (e.g. DYNABEADS™), radioactive label (e.g. $^{3}H$, $^{35}S$, $^{32}P$, $^{51}Cr$, or $^{125}I$), fluorescent label (e.g. fluoroscein, rhodamine, Texas Red, etc.), electron-dense reagents (e.g. gold), enzymes (e.g. alkaline phosphatase, horseradish peroxidase, or others commonly used in an ELISA), digoxigenin, or haptens and proteins for which antisera or monoclonal antibodies may be available (for example the peptides of the present invention can be made detectable by, for example, incorporating a radiolabel into the peptide, and used to detect antibodies specifically reactive with the peptide). The Variant SH2 of the invention may be provided with, a carrier such as for example coupled to bovine serum albumin (BSA) or keyhole limpet haemocyanin. The variant SH2 may be covalently or non-covalently coupled to a solid carrier such as a microsphere of gold or polystyrene, a slide, chip or to a wall of a microtitre plate. The variant SH2 may be labelled directly or indirectly with a label selected from but not limited to biotin, fluorescin and an enzyme such as horseradish peroxidase.

The particular label used may not be critical to the present invention, so long as it does not interfere with the affinity of the SH2 variant for the pTyr. However, in one embodiment, the imaging component may be a radionuclide (e.g. $^{18}F$, $^{11}C$, $^{13}N$, $^{64}Cu$, $^{68}Ga$, $^{123}I$, $^{111}In$, $^{99m}Tc$, etc.) due to the ease of using such techniques as SPECT, CT and PET imaging for in vivo detection of SH2 variant-pTyr complexes and tumor cells. Decision as to appropriate imaging component for agents used in SPECT or PET imaging may also be determined by whether the radionuclide is generated by generator or cyclotron or is an chelator or organic/halide.

A direct labelled probe, as used herein, may be a probe to which a detectable label is attached. Because the direct label is already attached to the probe, no subsequent steps may be required to associate the probe with the detectable label. In contrast, an indirect labeled probe may be one which bears a moiety to which a detectable label is subsequently bound, typically after the SH2 variant peptide is bound with the target pTyr.

In another embodiment, monoclonal antibodies (mab) which recognize any of the variant SH2 of the invention may also be made and used to detect the presence of the variant SH2 in a sample. Mab may provide a rapid and simple method of testing the compositions of the invention for their quality. In general, methods for the preparation of antibodies are well known. For example, methods to produce mab which specifically recognize the Variant SH2 of the invention are well known to those of skill in the art. In general, peptides are injected in Freund's adjuvant into mice. After being injected 9 times over a three week period, the mice spleens are removed and re-suspended in phosphate buffered saline (PBS). The spleen cells may serve as a source of lymphocytes, some of which may be producing antibody of the appropriate specificity. These may then fused with a permanently growing myeloma partner cell, and the products of the fusion may be plated into a number of tissue culture wells in the presence of a selective agent such as HAT. The wells may then be screened to identify those containing cells making useful antibody by ELISA. These may then be freshly plated. After a period of growth, these wells may again be screened to identify antibody-producing cells. Several cloning procedures may be carried out until over 90% of the wells contain single clones which are positive for antibody production. From this procedure a stable lines of clones may be established which produce the mab. The mab may then be purified by affinity chromatography using Protein A or Protein G Sepharose (see also, U.S. Pat. Nos. 4,609,893; 4,713,325; 4,714,681; 4,716,111; 4,716,117; and 4,720,459).

Research

In one embodiment, the variant SH2 domains of the present invention may be used as reagents. In particular embodiments, a variant SH2 domain, or a gene that encodes the variant SH2 domain, may be introduced into a mammalian cell line. A variant SH2 domain that exhibits super-high affinity to a target pTyr site (Kd value smaller than about 10 nM) may act to mask the target pTyr site and may cause severe blocking effects of PTK signalling events downstream of the pTyr site. Therefore, such variant SH2 domains may serve as an inhibitory reagent of cellular PTK signalling pathway. Super-high affinity variant SH2 domains derived from different natural SH2 domains exhibit distinct sequence recognition specificity. Consequently, a super-high affinity variant SH2 domain, when introduced in a live cell, may block a specific signalling pathway, and may be used as a reagent for investigating physiology of a particular pathway.

SH2 variants of the present invention having super-high affinity for pTyr may be used as substitutes for an anti-pTyr antibody and may be used in research areas where an anti-pTyr antibody is used, such as, for example, Western blots, IF, proteomics (enrichment of phosphoproteins/peptides), and so forth.

In one embodiment, variant SH2 domains which exhibit moderately enhanced affinity (variants that show enhanced affinity compared to the wild type, but preferably with a Kd value grater than about 10 nM to a target pTyr site) may be produced in accordance to the present invention. These variant SH2 domains do not have an ability to completely block a pTyr site and its downstream signalling, but they may retain inherent sequence recognition specificity of a parent SH2 domain to which amino acid substitutions are applied. Therefore, these variant SH2 domains may be used as tracers of particular tyrosine phosphorylation events in cells. To detect the tracer SH2 domain in cells, the SH2 domain may preferably be labelled with a probe molecule, as explained above.

Purification, Presence and Concentration of pTyr-Containing Targets

Another embodiment of the present invention includes the use of the variant SH2 polypeptides of the present invention as ligands for isolation, purification, detecting the presence and/or determination of the concentration of molecular targets having a pTyr in a sample. In one embodiment, a method for determining the presence/concentration of a target having a pTyr in a sample may comprise: (a) contacting the sample to a variant SH2 peptide of the present invention (the "SH2 ligand"), such that a target/SH2 ligand complex is formed if the target is present in the sample; and (b) determining the concentration of the pTyr-containing target in the sample by measuring the amount of target/SH2 ligand complex formed.

In another embodiment, the present invention provides for a method for isolating a pTyr-containing target in a sample. The method may comprise: (a) contacting the sample to a SH2 ligand of the present invention, such that a pTyr-containing target/SH2 ligand complex is formed if the target is present in the sample; and (b) releasing the pTyr containing target from the complex, thereby isolating the pTyr-containing target. The concentration of the target in the sample may then be obtained by measuring the amount of pTyr-containing target released.

In aspects, the SH2 ligand may be immobilized on a resin, such as an affinity column, and the sample, which may include fluids such as bodily fluids and extracts, may be passed through the resin. In aspects, the resin may be washed with a solution free of target. The pTyr-containing target bound to the SH2 ligand may be released by adding a solvent that removes the ability for the SH2 ligand to bind to the target thereby creating elution fractions. The presence and/or concentration of the target present in the elution fractions may be determined by any appropriate method, such as, for example, fluorescence, high performance liquid chromatography, and so forth. This method may also be used to isolate a pTyr-containing target from a sample. The SH2 ligand may also be bound onto a lateral flow strip.

The presence or concentration of pTyr-containing molecules such as peptides, including polypeptides and proteins, may be determined through high performance liquid chromatography (HPLC). The SH2 ligand may be bound to an affinity column or onto a lateral flow strip.

In one embodiment of the present invention the variant SH2 may be used in methods to identify cells with enhanced protein phosphorylation relative to a control. One such method may comprise using one or more of the variant SH2 to detect for the presence of pTyr-positive cells in a sample.

Advantages

Advantages of the present invention include:

(1) Unlike anti-pTyr antibodies, the variant SH2 peptides of the present invention are single polypeptides with relative smaller size (~12 kDa) than antibody, that are suitable as molecular drugs or reagents, and with the ability to work inside a live cell, like natural SH2 domains that function in cytoplasm. In addition, unlike the pTyr-specific antibody, a variant SH2 peptide of the present invention is equipped with sequence recognition specificity, and therefore it can detect only specific pTyr-containing molecules as targets of intervention.

(2) Another advantage of using an SH2 domain of the present invention includes ease of production and modification of the domain. An SH2 domain comprises ~100 amino acid residues and is suitable for recombinant protein production in a standard expression system including bacterial, yeast, and mammalian cells. In particular, about two-third out of 120 human SH2 domains were reportedly produced in *Escherichia coli* as a recombinant form (Huang et al. 2008, Mol Cell Proteomics, Vol. 7, pp. 768; Machida et al. 2007, Mol Cell, Vol. 26, pp. 899). Virdee et al. reported synthesis of an SH2 domain and incorporation of a non-natural amino acid by conjugating multiple polypeptide fragments (Virdee et al. Chemistry & Biology, 2010, Vol. 17, pp. 274). The cell-free expression system has also been used for production of SH2 domains (He and Taussig, 2007, Biochem Soc Trans, Vol. 35, pp. 962; Scott et al. 2004, J Biomol NMR, Vol. 30, pp. 463). The amino acid substitutions proposed herein are fully compatible to be incorporated into existing SH2 domain production technologies, including those mentioned above.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Example 1

Identification of Variant SH2 Domains by the Phage Display Technology

The amino acid residues of 15 positions on the human Fyn SH2 domain were randomly substituted to one of 20 natural amino acids to identify variant SH2 domains that bind to pTyr-containing peptides. All amino acid residue numbers of the human Fyn SH2 domain are in accordance with the full-length Isoform 1 of the UniProt database entry FYN_HUMAN. A gene that encodes the wild type Fyn SH2 domain between Ala139 and Gly249, the amino acid sequence of which is provided in SEQ ID NO: 1, was subcloned into the pDEST15 vector (Invitrogen Canada Inc.). The three cysteine residues in SEQ ID NO:1 were replaced with serine residues by the QuikChange II site directed mutagenesis kit (Qiagen Inc.). This mutagenesis generated a gene provided in SEQ ID NO: 2. The gene shown in SEQ ID NO:2 encodes a protein sequence provided in SEQ ID NO: 3. SEQ ID NO:3 comprises a fragment of the wild type human Fyn SH2 domain between Ala139 and Leu238, continued by a polypeptide sequence SSRLV-VPSHKG (SEQ ID NO: 25), in which the three serine residues were replaced from cysteine residues present in SEQ ID NO: 1. The gene provided in SEQ ID NO: 2 was fused to the gene encoding the M13 bacteriophage major coat protein. Simultaneous randomization on the pre-defined 15 amino acid positions, specified below, was performed with the Kunkel method (Sidhu, et al. 2000, Method Enzymol. Vol. 328, pp. 333). These 15 positions correspond to wild-type, full-length human Fyn SH2 residues Arg156 (position 1), Lys157 (position 2), Ala159 (position 3), Arg176 (position 4), Ser178 (position 5), Glu179 (position 6), Thr180 (position 7), Thr181 (position 8), Ala184 (position 9), Ser186 (position 10), Leu187 (position 11), Ser188 (position 12), Lys201 (position 13), His202 (position 14), and Lys204 (position 15) (FIG. 2a). In SEQ ID NO:1 these 15 positions are as follows: Arg18 (position 1), Lys19 (position 2), Ala21 (position 3), Arg38 (position 4), Ser40 (position 5), Glu41 (position 6), Thr42 (position 7), Thr43 (position 8), Ala46 (position 9), Ser48 (position 10), Leu49 (position 11), Ser50 (position 12), Lys63 (position 13), His64 (position 14), and Lys66 (position 15). The mutagenesis generated a library of Fyn SH2 domains that contain randomly substituted amino acid residues on the 15 positions. The phage display method was employed to display these Fyn SH2 domains that incorporated the substitutions, on the surface of M13 bacteriophage. The phages were screened against 33 immobilized pTyr-containing synthetic peptides listed in FIG. 3. Each peptide was synthesized on the TentaGel amide resin (INTAVIS Inc.) and N-terminally labeled with biotin. Phages that bound to at least one of these peptides were forwarded to DNA sequencing, to identify sequences of variant SH2 domains that bound to a peptide. Accordingly, 63 variant Fyn SH2 domains were identified. The residues on the 15 positions in each variant SH2 domain are listed in FIG. 4. In each variant, at least one position contained an amino acid substitution from the wild-type residue, which are shaded black in FIG. 4. No variant SH2 domain was identical to the wild-type SH2 domain that has SEQ ID NO:3. This indicates that all of the variant SH2 domains gained more favorable sequence composition for enhanced binding to pTyr-containing peptides compared to the wild-type SH2 domain. Substitutions observed in the variant SH2 domains are listed together in FIG. 5. Therefore, we identified amino acid substitutions, applied to an SH2 domain, that enhance binding to pTyr-containing polypeptides.

Example 2

Enhanced Binding of Variant Fyn SH2 Domains to pTyr-containing Peptides In Vitro Single or multiple substitutions were introduced to the wild-type Fyn SH2 domain and determined degrees of affinity enhancement derived by introduction of the substitutions. The gene of SEQ ID NO: 2 was N-terminally fused with a gene coding a hexa-histidine tag, which resulted in a construct that expresses SEQ ID NO: 4, which includes a hexa-histidine tag, the wild type Fyn SH2 domain corresponding to the region between Ala139 and Leu238, continued by a polypeptide with a sequence SSRLVVPSHK-GAAA (SEQ ID NO: 26). Using this wild-type construct as a template, 13 variant Fyn SH2 domains were constructed, by the directed mutagenesis method. In following descriptions, position numbers are used to specify residues to be substituted. For example, T8V indicates a substitution of Thr at position 8 to Val, applied to the wild type construct. In another example, T8V/S10A/K15L indicates a combination of three substitutions, Thr at position 8 to Val, Ser at position 10 to Ala, and Lys at position 15 to Leu, applied to the wild-type construct. Amino acid sequences between position 1 and position 15, of the 13 variant SH2 domains are listed in the SEQUENCE LISTING section. By applying substitutions to the wild type construct (SEQ ID NO:4), following variant Fyn SH2 domains were constructed: T8V (SEQ ID NO:5), S10V (SEQ ID NO:6), Δ8/S10A/K15L (SEQ ID NO:7), S10A (SEQ ID NO:8), K15L (SEQ ID NO:9), S10V/K15L (SEQ ID NO:10), K2E/T8V/S10A/K15I (SEQ ID NO:11), T7S/S10A/K15L (SEQ ID NO:12), S10A/K15L (SEQ ID NO:13), T8V/S10A/K15I (SEQ ID NO:14), T8V/K15L (SEQ ID NO:15), T8I/S10A/K15L (SEQ ID NO:16), and T8V/S10A/K15L (SEQ ID NO:17). ΔT8 denotes deletion of Thr at position 8.

A set of peptides that contain pTyr, and one peptide that does not contain pTyr, were synthesized for binding assay (FIG. 6). Each peptide was synthesized on the TentaGel amide resin (INTAVIS Inc.) and N-terminally labeled with fluorescein using NHS-fluorescein (Thermo Fisher Scientific). Each of the 13 variant and the wild-type SH2 domain was produced by overexpression in the *Escherichia coli* BL21(DE3) strain cultured in LB media (EMD Chemicals). Expression was induced by 0.3 mM isopropyl β-D-1-thiogalactopyranoside (IPTG), and the cell culture was incubated for 5 hours at 37° C. The cells were harvested by centrifuge, and broken on ice, in buffer solution containing 20 mM sodium phosphate, 0.1 M NaCl, 20 mM imidazole, 1 mg/ml lysozyme and 1% Triton-X 100, adjusted at pH 7.8. Affinity purification was performed with the Ni-NTA agarose resin (Qiagen Inc.), according to the manufacturer's instruction. The purified material was dialyzed against phosphate-buffered saline (PBS), pH 7.4, at 4° C. overnight. Measurements of fluorescence polarization were conducted by titrating the SH2 domain concentration, while keeping the peptide concentration constant. Kd values were calculated with the GraphPad Prism software, by assuming the one-site binding model (GraphPad Software).

Figure 8:
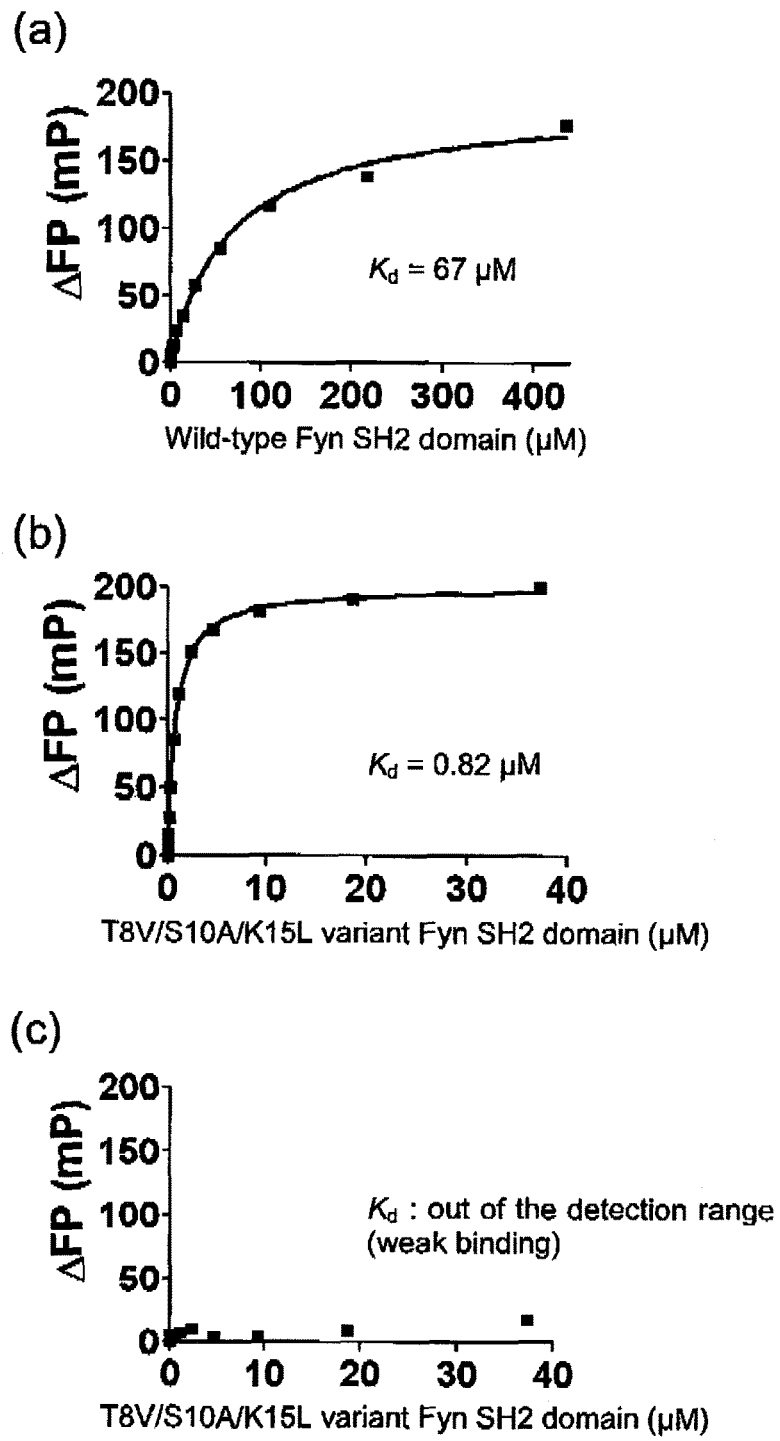
FIG. 8 shows binding curve and Kd values of the wild-type or variant Fyn SH2 domain to a peptide, measured by increase of fluorescein polarization (ΔFP).

The determined Kd values of interaction between the 14 SH2 domains (including the wild-type) and seven peptides were listed in FIG. 7(a). Fold increase of affinity enhancement was calculated as Kd[wild-type] divided by Kd[variant], and listed in FIG. 7(b). Compared to the wild type Kd values, which range between the orders of $10^{-5}$ M and $10^{-7}$ M (submicromolar affinity), Kd values of the T8V/S10A/K15L variant SH2 domain range between the orders of $10^{-7}$ M and $10^{-9}$ M (nanomolar affinity) to the same set of seven peptides (FIG. 7(a)). In average, this corresponds to 293-fold affinity increase (FIG. 7(b)). In particular, binding to the EGFR-pY978 peptide showed over 1000-fold affinity increase. The inventors also compared binding of the wild-type and the T8V/S10A/K15L variant SH2 domains to a short pTyr-containing peptide, the GGpYGG peptide (SEQ ID NO: 23). Affinity to this peptide increased from a Kd value of 67 μM (FIG. 8(a)) to 0.82 μM (FIG. 8(b)). However, the non-phosphorylated peptide, the GGYGG peptide (SEQ ID NO: 24), did not show detectable binding to the same variant SH2 domain (FIG. 8(c)). This indicates that the combination of three substitutions, namely T8V, S10A, and K15L, contributes to enhancement of binding to the pTyr amino acid included in the tested peptides. Therefore, the inventors created a variant SH2 domain that demonstrated significantly enhanced affinity to pTyr-containing peptides.

In addition to the abovementioned variant SH2 domain, 12 other variant SH2 domains also showed enhanced affinity to the seven peptides. Each of these variant SH2 domains contains different single of multiple substitutions, selected from the amino acid substitution list appeared in FIG. 5. It was shown that different substitutions resulted in different degrees of affinity enhancement. In average, the effect of enhancement ranges between 1.4-fold (the T8V variant) to 86.4-fold (the T8I/S10A/K15L variant) increase (FIG. 7(b)). Therefore, the inventors obtained a panel of variant SH2 domain that produced a gradient of affinity enhancement to pTyr-containing peptides.

Example 3

Affinity Enhancement Observed by Introducing Substitutions to the Src SH2 Domain In this section, the inventors demonstrate that the substitutions established on the human Fyn SH2 domain also worked on another SH2 domain for affinity enhancement.

The gene encoding the human Src SH2 domain between Asp144 and Lys252, residue numbers of which are in accordance with the UniProt entry SRC_HUMAN, was subcloned into the vector pETM-11 (Dümmler, et al. 2005, Microb Cell Fact., Vol. 4, pp. 34). The resultant construct encodes a protein of SEQ ID NO:18, which comprises an N-terminal hexa-histidine affinity tag, a Tobacco Etch Virus protease cleavage site, and the Src SH2 domain. Next, a sequence alignment that contains the sequences of the human Fyn and Src SH2 domains was generated using the program PROMALS3D (Pei, et al., 2008, Nucleic Acids Research, Vol. 36, pp. W30) (FIG. 2a). The 15 positions were identified on the wild-type Src SH2 domain sequence, based on the aligned positions defined on the Fyn SH2 domain. For example, in the Src SH2 domain sequence, Thr183 corresponds to position 8, Cys188 corresponds to position 10, and Lys206 corresponds to position 15. Expression constructs for three variant Src SH2 domains were created by site directed mutagenesis. The polypeptide sequences for the region between position 8 and position 15 for each of the three variant Src SH2 domains were listed in the SEQUENCE LISTING, where SEQ ID NO:19 corresponds to the K15L variant SH2 domain, SEQ ID NO:20 corresponds to the T8V/C10A variant SH2 domain, and SEQ ID NO:21 corresponds to the T8V/C10A/K15L variant SH2 domain. The three amino acid residue substitutions, a residue at position 8 to Val, a residue at position 10 to Ala, and a residue at position 15 to Leu, are derived from the list of favorable substitutions, originally elucidated from the Fyn SH2 domain phage display experiments (FIG. 5).

The wild-type and variant Src SH2 domains were expressed in *E. coli* BL21(DE3) strain grown in the LB media, by inducing protein expression with 0.3 mM IPTG, and incubating the cell culture at 30° C. for six hours. Cells were harvested by centrifuge, and broken on ice in buffer solution containing 20 mM sodium phosphate, 0.1 M NaCl, 20 mM imidazole, 1 mg/ml lysozyme, 1% Triton-X 100, adjusted at pH 7.8. Affinity purification was performed with the Ni-NTA, agarose resin, according to the manufacturer's instruction. The materials eluted from the resin were dialyzed against buffer solution containing 20 mM Tris-HCl, pH 7.0, 1 mM dithiothreitol (DTT), 0.5 mM ethylendiaminetetraacetic acid (EDTA), and 50 mM NaCl, at 4° C., overnight. Each of the dialyzed samples was supplemented with the Tobacco Etch Virus protease (Tropea, et al. 2009, Methods Mol Biol. Vol. 498, pp. 297), for cleavage of the hexahistidine tag, and incubated at room temperature, overnight. The samples were further purified with the Superdex75 size exclusion column (GE Healthcare), with buffer solution comprising 20 mM Tris-HCl, pH 7.0, 1 mM DTT, and 150 mM NaCl.

Fluorescence polarization assay was conducted to determine Kd values of the interaction between the wild-type or variant Src SH2 domain and seven fluorescein-labeled pTyr-containing peptides (FIG. 9a). Fold increase of Kd values was calculated and listed in FIG. 9b. All the three variant SH2 domains showed affinity increase compared to the wild type SH2 domain. The T8V/C10A/K15L variant Src SH2 domain bound to three peptides, namely the EGFR-pY978, MidT-pY324, and ShcA-pY239 peptides, with Kd values in the order of 10-9 M (nanomolar affinity). This variant Src SH2 domain showed an average of 238-fold affinity increase from the wild type SH2 domain. This amount of affinity increase is similar to the 293-fold affinity increase demonstrated for the T8V/S10A/K15L variant Fyn SH2 domain (FIG. 7(b)). Furthermore, the T8V/C10A/K15L variant Src SH2 domain showed binding to the GGpYGG peptide (SEQ ID NO: 23) with a Kd value of 0.51 μM, which indicates much higher affinity than the wild type Src SH2 domain to the peptide (FIG. 10). Therefore, the combination of three substitutions, a residue at position 8 to Val, a residue at position 10 to Ala, and a residue at position 15 to Leu, applied to different SH2 domains, which resulted in similar significant effects of affinity enhancement to pTyr-containing peptides.

Example 4

Binding of Variant SH2 Domains to EGFR and Inhibition of Downstream Signaling in Mammalian Cells Binding of the epidermal growth factor (EGF) induces dimerization of a receptor tyrosine kinase, the EGF receptor (EGFR), and trans-autophosphorylation on multiple tyrosine residues in the C-terminal tail. These pTyr-containing sites recruit downstream proteins that contain an SH2 domain, including Grb2. Deregulation in the expression or activity of EGFR is associated with many epithelial cancers. The MAP kinase pathway (the Ras-Raf-MEK-Erk protein signalling), when activated downstream of EGFR, leads to cell proliferation; however, when over-activated, it leads to cellular transformation or invasive behaviour (Kim & Choi, (2010) Biochimica et biophysica acta, Vol. 1802, pp. 396). Here, we further demonstrate that the substitutions defined on the Fyn SH2 domain worked on other SH2 domains for affinity enhancement. In addition, the variant SH2 domains created from different parent SH2 domains, when expressed in mammalian cells, showed enhanced binding to EGFR. Furthermore, the variant SH2 domains expressed in mammalian cells inhibited cellular signaling events downstream of EGFR.

The gene encoding a polypeptide between Met55 and Pro158 of the human Grb2, where the residue numbers are in accordance with the UniProt entry GRB2_HUMAN, was subcloned into the pEGFPC2 vector using the XhoI and BamHI restriction sites. The amino acid sequence of Grb2 was aligned with the Fyn sequence, to identify positions on the Grb2 sequence (FIG. 2(a)). Accordingly, amino acid residues at position 8, 10, and 15 were identified as Ala91, Ser96, and Lys109, respectively. These residues at the three positions were substituted with Val, Ala, and Leu, respectively, using the site-directed mutagenesis method, to generate a construct of the A8V/S10A/K15L variant Grb2 SH2 domain, the sequence of which, comprising the region between Met55 and Pro158 with the A8V, S10A, and K15L substitutions, was shown in SEQ ID NO: 22.

The genes encoding the wild-type Fyn SH2 domain, the wild-type Src SH2 domain, the wild-type Grb2 SH2 domain, the T8V/S10A/K15L variant Fyn SH2 domain, the T8V/C10A/K15L variant Src SH2 domain, and the A8V/S10A/K15L variant Grb2 SH2 domain were, respectively, subcloned into the pEGFPC2 vector (Clontech) using the XhoI and BamHI restriction sites.

Figure 11:
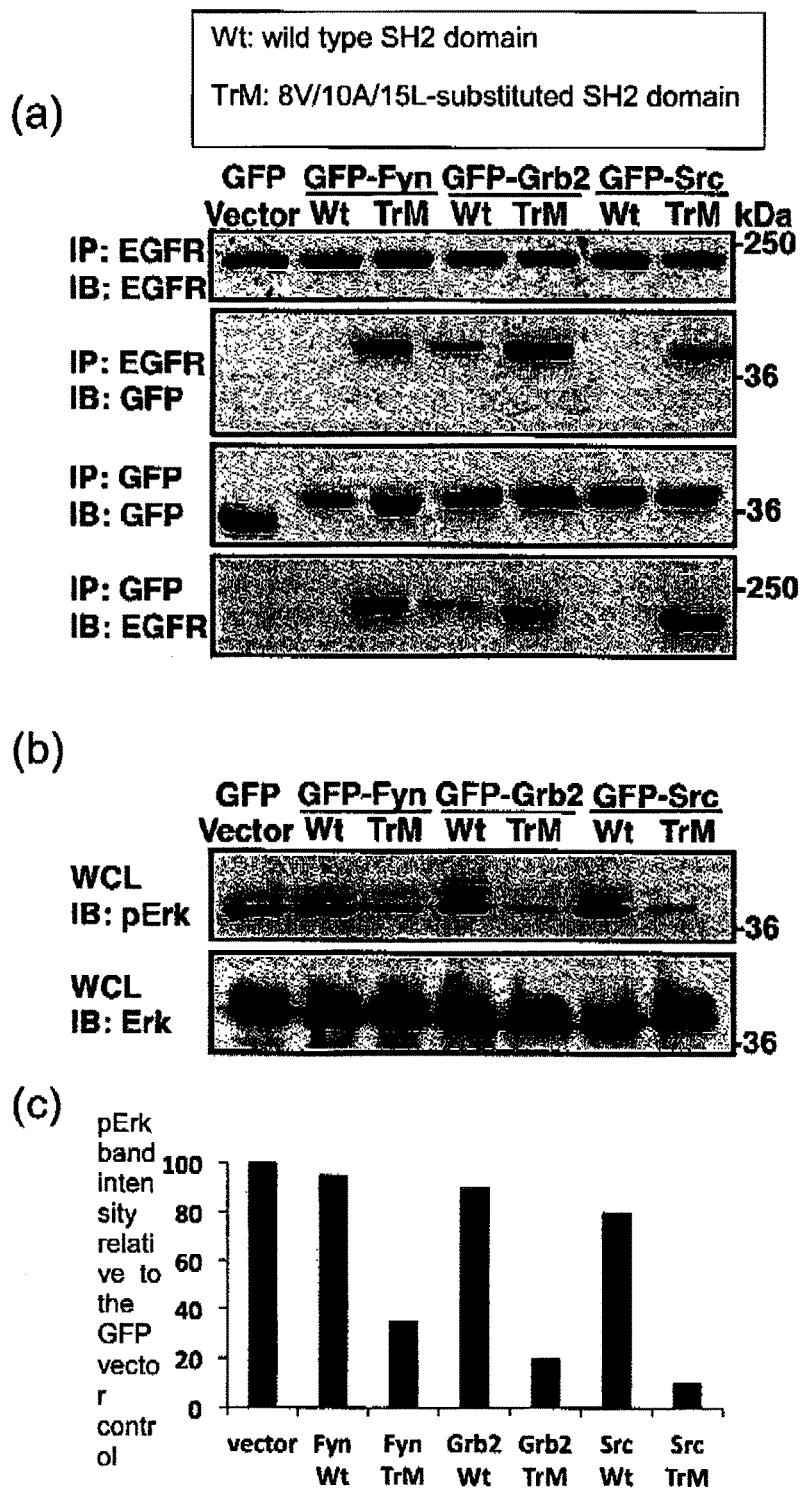
FIG. 11 shows effects of the 8V/10A/15L-substituted Fyn, Grb2 and Src SH2 domains (designated as TrM) in comparison with wild-type (designated as Wt) domains in cellular signalling downstream of EGFR. SH2 domains are fused with GFP and expressed in HEK293 cells.
Figure 12:
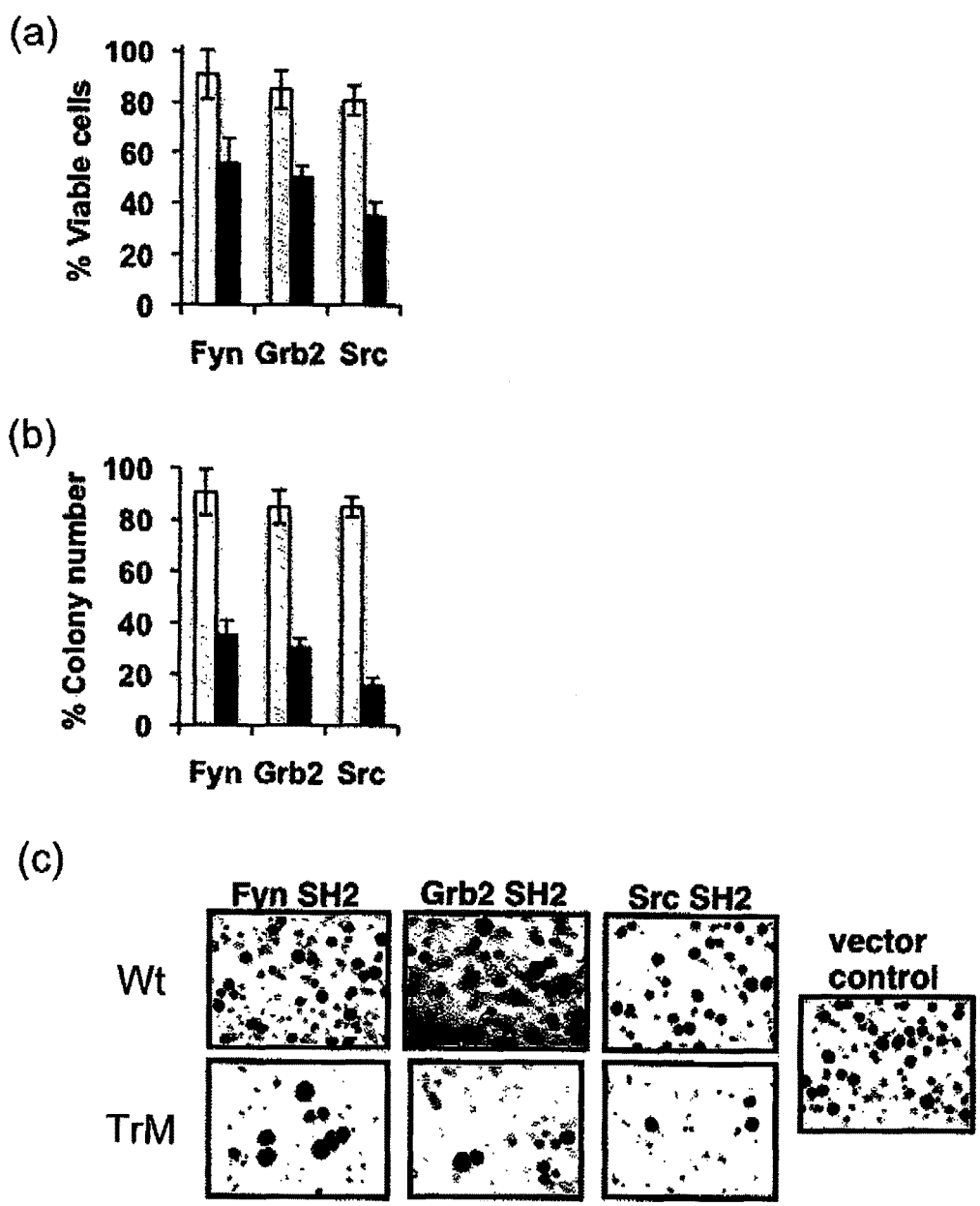
FIG. 12 shows inhibitory effect of the TrM (8V/10A/15L-substituted) SH2 domains to the growth of HEK293 cells. The SH2 domains were expressed as a GFP fusion protein in HEK293 cells.

The three variant SH2 domains mentioned in the previous sentence were dubbed as 8V/10A/15L-substituted SH2 domains, or the TrM SH2 domains, in the following descriptions, as well as in FIG. 11 and FIG. 12. The wild-type (Wt) and TrM SH2 domains, subcloned into the pEGFPC2 vector, were expressed in the HEK 293 cells as a GFP-fusion protein. Methods used in this and the following sections are described below.

Anti-GFP rabbit polyclonal antibody was purchased from Sigma-Aldrich. Anti-EGFR rabbit polyclonal antibody was purchased from Millipore. Anti-p44/42 MAPK (Erk1/2) mouse monoclonal antibody, and anti-phospho-p44/42 MAPK (Thr202/Tyr204) mouse monoclonal antibody were purchased from Cell Signaling. HEK 293 cells were grown in Dulbecco's modification of Eagle's medium (DMEM, Sigma-Aldrich) supplemented with 10% fetal bovine serum (FBS, SAFC Biosciences), 50 units/ml penicillin and 50 μg/ml streptomycin (GIBCO Invitrogen Corp.) in a humidified atmosphere of 5% CO2 in air at 37° C. EGF (Invitrogen) at a final concentration of 100 ng/ml was added to the medium at the indicated time point. Transient transfections were carried out with jet-PEI (PolyPlus-Transfection; Illkirch, France) according to manufacturer's instruction.

HEK 293 cells were transfected with the SH2 domain construct subcloned in the pEGFPC2 vector, and incubated in serum-containing full medium for 24 h followed by serum-starvation for 16 h and then EGF (100 ng/ml) treatment for 10 min, pervanadate treatment for 10 min. The whole cell lysates were prepared and subjected to IB analysis to detect phosphorylated Erk and total Erk.

HEK 293 cells were lysed with cold lysis buffer (1% NP-40, 50 mM Tris-HCl pH 7.4, 150 mM NaCl, 2 mM EDTA, 50 mM NaF, 10% Glycerol and protease inhibitor cocktail diluted at 1:1000). After centrifugation at 13,000*g for 15 min, the supernatants were collected. After clearance of the lysate with appropriate pre-immune serum and protein G (Roche), immunoprecipitation (IP) and immunoblotting (IB) were performed.

All TrM SH2 domains tagged with GFP bound significantly to the EGFR (FIG. 11(a)). The binding was observed with immunoprecipitation (IP) assay using the anti-GFP and anti-EGFR antibodies. On the contrary, the Wt Fyn and Src SH2 domains did not show detectable binding to EGFR. Weak binding of the Wt Grb2 SH2 domain was observed, which is reasonable because EGFR is a physiological binding target of the Grb2 SH2 domain. Similar to the TrM Fyn and Src SH2 domain, the TrM Grb2 SH2 domain exhibited strong binding to EGFR, with significantly higher affinity than the Wt Grb2 SH2 domain, Therefore, we demonstrated that our strategy of affinity enhancement worked efficiently by applying it to the Grb2 SH2 domain.

Next, we observed effects of expression of TrM SH2 domains towards signaling events downstream of EGFR in mammalian cells. The phosphorylation level of the downstream protein Erk was observed by Western blotting with anti-phospho-Erk (pErk) antibody. Significant reduction of the pErk level was observed for HEK293 cells that express TrM SH2 domains, compared to Wt SH2 domains (FIG. 11(b), FIG. 11(c)). This indicates that activation of the MAP kinase pathway, located downstream of EGFR, was blocked by expression of the TrM SH2 domain in the cells. Therefore, we demonstrated that tight binding of a TrM SH2 domain to EGFR blocked activation of downstream signaling.

Example 5

Inhibitory Effects of TrM SH2 Domains Observed on Cell Growth and Colony Formation To examine effects of the TrM SH2 domains on cell growth, HEK 293 cells were transfected with the pEGFPC2-SH2 domain construct plasmid, as described previously, and then incubated in full medium with EGF (100 ng/ml) for 36 h. Cells were trypsinized and stained using 0.4% trypan blue (Sigma-Aldrich) and viable and total cell numbers were counted in haemacytometer with the use of a microscope according to manufacturer's instruction. FIG. 12(a) shows the number of viable cells relative to the empty vector control. Expression of the TrM SH2 domains resulted in reduction of viable cells, compared cells expressing the Wt SH2 domains. This observation demonstrated that the TrM SH2 domain has inhibitory effects that slow down proliferation of cells.

To examine the effect of the TrM SH2 domains on anchorage-independent cell growth, which is an indicator of tumorigenicity, soft agar assay was performed according to the method described by Howard et al. (Proc Natl Acad Sci, 2003, Vol. 100, pp. 11267). HEK293 cells were transfected with the pEGFPD2-SH2 domain constructs by PEI and grown overnight. On the following day, cells were trypsinized and plated at a density of 1×104 cells in 0.25% agarose in DMEM (10% FBS) on top of 0.5% agarose in DMEM (10% FBS) in 60 mm dishes in triplicates. Cells were maintained at 37° C. in 5% CO2 for 21 days, and stained overnight with 3-(4,5-dimethylthiazol-2-yl)-2,5-diphenyl-tetrazolium bromide. FIG. 12(b) shows the number of colonies expressing Wt or TrM SH2 domains, relative to the numbers with empty vector control cells. FIG. 12(c) shows example photos taken from each sample. Therefore, TrM SH2 domains demonstrated inhibitory effects on colony formation in soft-agar, which suggests that the TrM SH2 domains can be used as anti-cancer agents.

Example 6

SH2 Variants as In Vivo Robes of EGFR Signalling

Cellular signalling is highly dynamic[21]. However, there are few experimental tools that allow monitoring of these dynamic events in a non-invasive manner. Profiling of phosphorylation dynamics using phospho-specific antibodies[23] or mass spectrometry (MS)[21] can only obtain snapshots of signal transduction because cells must be processed for immunostaining or MS analysis. SH2 domain variants offer an alternative by which to examine dynamic signalling events in real time and live cells.

Two important considerations for developing in vivo signalling probes are specificity and affinity. Natural SH2 domains bind their cognate pTyr-containing target polypeptides with moderate specificity and affinity. Using phage displayed libraries according to the present invention allows obtaining SH2 variants with desired properties. The objective in this example is to create a panel of SH2 variants that exhibit defined specificities towards pTyr sites in the EGFR, and desired affinities with an optimized pTyr-binding pocket. This panel of "tailor-made" SH2 variants are expressed in cells as fusions to VP (i.e. GFP, YFP or CFY). SH2-XFP fusion can be expressed in A431, a human epithelial carcinoma line that express high levels of EGFR, and monitor its localization to the plasma membrane upon EGF stimulation by live cell imaging[21]. The use of one SH2 probe will reveal the dynamic phosphorylation profile of a single site. The use of multiple orthogonal probes would permit the simultaneous monitoring of multiple pTyr sites during EGFR signalling. The studies with the SH2-XFP probes are complemented by multiple reaction monitoring (MRM)-MS analysis[22] of site-specific tyrosine phosphorylation and by Western blots (WB) to examine the activation of the corresponding signalling pathways. Information on phosphorylation dynamics obtained in this example can help prioritize which pTyr sites and SH2 monobodies to test for cancer intervention as described below.

Example 7

SH2 Monobodies as Specific Inhibitors of ErbB Signalling and as Therapeutic Agents While antibody-based therapies show great promise in treating cancers, they have to be humanized to avoid fatal immunoreaction. Most patients become resistant to treatment after being in the antibody therapy for some time[20, 1-3], making it necessary to find alternative therapeutic strategies that can be used alone or in combination with existing therapies[4]. SH2 monobodies, which are based on human SH2 domains, are hypo-immunogenic[5]. Hypoimmunogenicity together with their relatively small size and high specificities towards pTyr sites, which are often amplified in cancer[6, 7], makes SH2 domain-based monobodies an attractive platform for developing molecular targeted cancer therapy. The present invention provides the ability to evolve and design SH2 variants with precise specificity and ultra-high affinity afford an unprecedented opportunity to exploit this potential.

A panel of SH2 variants/monobodies developed in previous examples is used as therapeutic candidates for breast cancer by testing the efficacy of an SH2 monobody in inhibiting ErbB receptor signalling and cell proliferation. Promising candidates are then evaluated in a 3D cell culture model of breast cancer. Finally, the best SH2 monobodies are evaluated in tumor xenografts in mice.

Example 8

SH2 Monobodies as Inhibitors of ErbB Signalling

Figure 13:
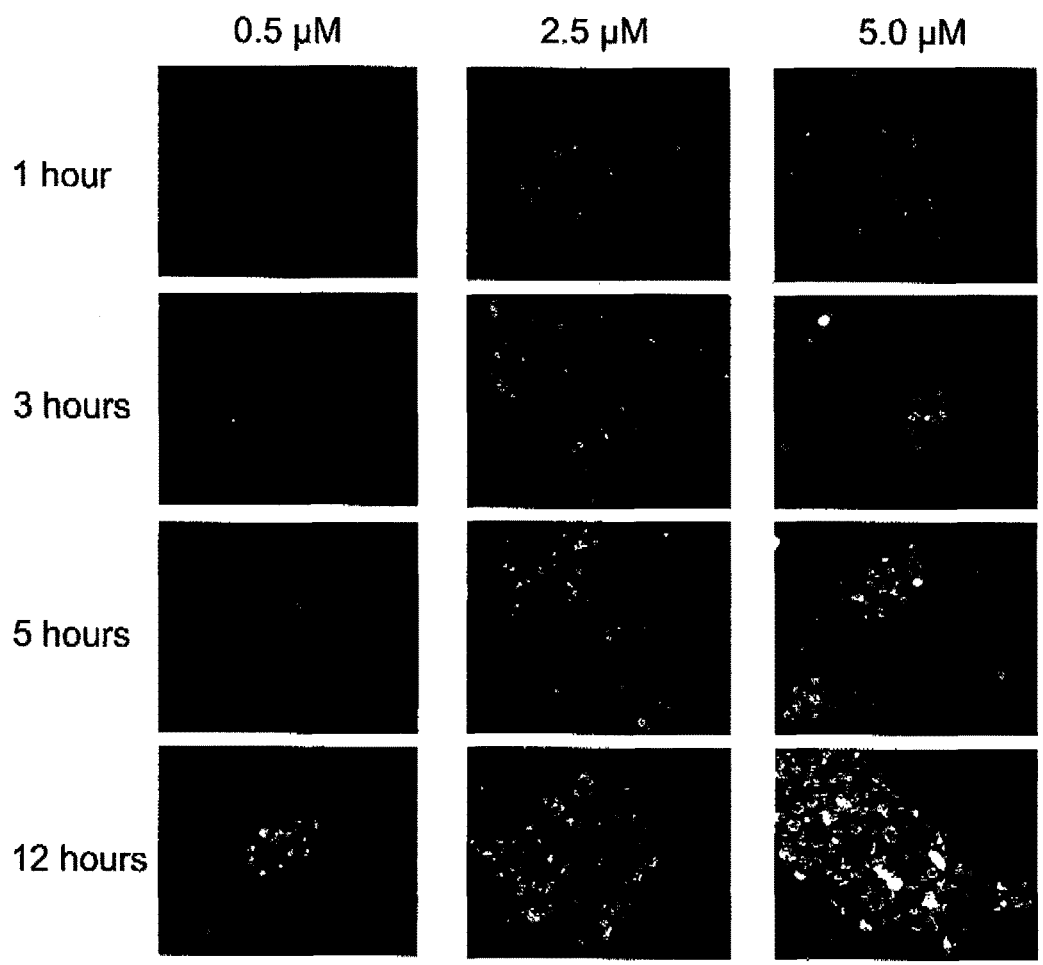
FIG. 13 are photographs showing transduction of TAT-SH2 protein in cells. Bacterial expressed, purified TAT-FynSH2 domain is labeled with FITC and incubated with HEK293 cells at the indicated concentration (columns) and time (rows). Effective protein transfusion is observed at 2.5 μM SH2 protein after 1 hr incubation.

Because the ErbB family, in particular ErbB1 (EGFR) and ErbB2, are frequently amplified in breast cancer[20], the super pTyr-binders developed in the examples herein can be employed to inhibit ErbB receptor signalling and cell proliferation in a relevant cell model. To this end, one can take advantage of the MCF10A-ErbB1 (or 10A-ErbB1) and MCF10A-ErbB2 (or 10A-ErbB2) created in the Muthuswamy lab[8-11]. Specifically, the mammary gland-derived MCF10A cells were made to stably express chimeric ErbB1 or ErbB2 receptor whose cytoplasmic domain is linked to the synthetic ligand-binding domain from FK506-binding protein (FKBP)[8-12]. The chimeric ErbB receptors can be dimerized and thereby, activated by the bivalent FKBP ligand AP1510[8-12]. The MCF10A, 10A-ErbB1 and 10A-ErbB2 cells can be transfected with plasmids encoding an wt or mutant SH2 domain or treated with an SH2 monobody fused to a TAT protein transduction domain[13-14]. Applicants have confirmed that purified TAT-SH2 domains (labelled with FITC) penetrate cells and have half-lives of 2-3 days in cell culture (FIG. 13). Following the stimulation with AP1510, the cells will be monitored for proliferation by the MTS assay[4] and for apoptosis by the TUNEL assay[4, 8-10]. Immunoprecipitation (IP) and WB experiments are also carried out to examine the activation of the Ras/MAPK growth pathway (ie., by measuring the phosphorylation of MEK1/2 and Erk1/2, respectively) and the PI3K/Akt survival pathway (i.e. by measuring Akt phosphorylation). For the group of SH2 monobodies showing an inhibitory effect to ErbB signalling and ErbB-dependent cell growth, similar studies will be carried out in other ErbB-overexpressing human breast tumour cell lines such as BT-474, SKBR-3 and MDA-361.

Example 9

SH2 Monobodies in 3D Culture

MCF10A cells, when plated on a bed of extracellular matrix, form 3D acinar structures resemble breast acini in vivo[8]. Breast cancer cells have been shown to form abnormal acinar structures characterized with aberrant morphology, enhanced proliferation and reduced apoptosis. These features are recapitulated by the 10A-ErbB2 cells[8, 10, 15]. Therefore, the MCF10A 3D culture system was used to further evaluate the SH2 monobodies. Specifically, MCF10A, 10A-ErbB1 and 10A-ErbB2 cells are cultured on matrigels in the presence or absence of different concentrations of AP1510 and/or TAT-SH2 monobodies following established protocols. The acinar organization at different stages of morphogenesis can then be determined by confocal analysis of DAPI-labelled structures. Cell proliferation and survival can be monitored by immunostaining for the Ki-67 (proliferation marker) and cleaved caspase-3 (apoptosis) or by TUNEL staining[4, 8, 9, 15, 16].

Example 10

SH2 Monobodies in Mouse Model of Breast Cancer

The efficacy of SH2 monobodies in inhibiting or slowing down mammary tumorigenesis can be evaluated in vivo in a mouse model of human breast cancer. For example by using the Comma-1D cells and the mammary fat pad transplantation system established in the Muthuswamy lab[9, 15]. CD cells stably expressing Erb1 or Erb2 are already available from the Muthuswamy lab[9]; these cells are injected into the epithelium-cleared mammary fat pad of 3-week old female BALB/c mice[9]. The tumor growth is measured weekly with digital callipers. Two complementary approaches are used to evaluate the SH2 monobodies in inhibiting tumour initiation and growth, respectively. For tumour initiation, CD cells that stably express both Erb2 (or Erb1) and an SH2 monobody (with a XFP tag for easy tracking are created. Upon transplantation, the ability of these cells in initiating mammary tumours is assayed in comparison to CD cells expressing the Erb2 or Erb1 alone. For tumour progression, mice transplanted with CD-ErbB2 or CD-ErbB1 cells are treated with TAT-SH2 monobodies when the tumour reaches a certain size (eg., ~150 mm3)[4]. A TAT-SH2 monobody (or a control SH2 domain) at different concentrations is injected intraperitoneally once a day for three weeks. As a control, the tumours are treated with Trastuzumab (Herceptin), an anti-ErbB2 antibody[4]. Tumor sizes are measured daily. At the end of the treatment, the mice are sacrificed and the tumour tissues fixed and stained with hematoxylin and eosin to evaluate histological changes117. TUNEL staining or immunostaining for cleaved caspase-3118 are used to investigate the apoptosis status of the tumours. Immunostaining for Ki67 and the proliferating cell nuclear antigen (PCNA) to assay for tumour proliferation[9, 18]. Biochemically, the tumor lysates are analyzed for the activation of Erk and Akt. Fyn/Src/Grb-SH2 triple mutants are used to establish the protocols for evaluating SH2 monobodies using the mouse breast cancer model and extend the study to include monobodies that exhibit the highest efficacy in blocking ErbB signalling in 2D and 3D cultures. The most effective SH2 monobodies can also be further validated in BT-474 xenografts established in nude mice[4].

Example 11

Figure 14:
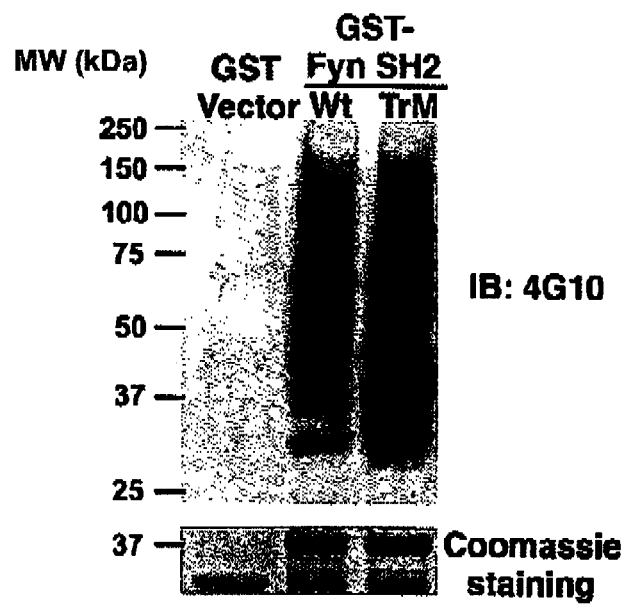
FIG. 14 shows enhanced ability of the Fyn TrM SH2 domain compared to the Wt SH2 domain for binding to tyrosine-phosphorylated proteins, as revealed by the glutathione S-transferase (GST) pulldown assay. IB: immunoblot. 4G10: antibody against pTyr (Millipore Co.). MW: molecular weight in the unit of kilodalton. The top panel shows the result of Western blotting after the pulldown assay. The bottom panel shows loading control of GST-tagged proteins immobilized on the glutathione sepharose beads (GE healthcare) as revealed by the Coomassie staining method.

GST Pulldown Assay for Binding Capacity Comparison of the TrM with the Wild-type (WT) SH2 Domain GST pulldown assay demonstrated that the TrM SH2 domain captures more tyrosine-phosphorylated proteins from cell lysate (FIG. 14).

The wild-type (Wt) and triple mutant (TrM) Fyn SH2 domains ($Ala^{139}$-$Gly^{249}$) were respectively subcloned into the pETM30 vector (Dümmler, et al. Microb. Cell Fact. 4, 34 (2005)). The Fyn SH2 domain constructs contain a FLAG tag sequence (DYKDDDDKC) (SEQ ID NO: 27) at the C-terminus. To create the GST control vector, a stop codon was inserted after the GST tag sequence of the original pETM30 vector. The GST and GST-SH2 proteins were expressed in *E. coli* BL21(DE3). HeLa cells were treated with 50 μM pervanadate for 10 min at 37° C. HeLa cells were lysed on ice in lysis buffer containing 0.5% NP-40, 50 mM HEPES pH 7.4, 1 mM magnesium chloride, 150 mMKCl, and the COMPLETE protease inhibitor cocktail (Roche). The GST pulldown assay was conducted as described (Li et al. J. Biol. Chem. 278, 3852-3859 (2003)). The phosphoproteins were revealed by Western blot using the 4G10 anti-pTyr antibody (Millipore).

Example 12

Kinase Activation-dependent Detection of Anaplastic Lymphoma Kinase (ALK) by the Src SH2 TrM Receptor tyrosine kinases are activated by extracellular stimulation and phosphorylate intracellular substrates, including the cytoplasmic region of the kinase itself. Anaplastic lymphoma kinase (ALK) is a receptor tyrosine kinase, which is stimulated by the activation antibody mAb46. The H370 cell line is an HEK293 cell line stably expressing ALK. FIG. 15A demonstrates that SrcTrM can capture a substantially larger amount of phosphorylated proteins from H370 cell lysate upon stimulation, compared to the Wt.

The Wt human Src (hSrc) SH2, the TrM hSrc SH2, and Wt Rous sarcoma virus Src (vSrc) SH2 domains were prepared, respectively, as GST tag fusion proteins. The vSrc SH2 domain is almost identical to the hSrc SH2 domain (there are three-residue differences in the SH2 domain region, and the differences are located outside of the target-binding surface). 5 μg of the GST-tagged SH2 domain was incubated with 500 μg of H370 cell lysate treated with or without the ALK activation antibody mAb-46 at room temperature for 30 min. 20 μl of glutathione sepharose beads was then added for another 30 minincubation at room temperature. As a positive control, the anti-pTyr antibody P-Tyr-100 (Cell Signaling, #9411) was used for immunoprecipitation. 4 μl of the P-Tyr-100 antibody was incubated with 500 μg H370 cell lysate treated with or without the ALK activation antibody mAb-46 for 2 hours at 4° C. Next, 20 μl protein G beads was added for another incubation for two hours at 4° C. The glutathione beads or protein G beads were washed with 1×PBS (phosphate buffered saline) three times. The beads were added to 30 μl 2×SDS loading buffer and boiled for 10 min. The samples were resolved on an 8% Bis-Tris SDS-PAGE gel. The gel was applied to Western blotting to transfer the samples onto PVDF membrane (Millipore) and the proteins were probed with the P-Tyr-100 antibody. The major bands (220 kDa and 140 kDa) shown on the Western blots are two species of ALK (FIG. 15A).

In FIG. 15B, the Src SH2 TrM was further demonstrated to function as a probe to detect tyrosine-phosphorylated proteins on a PVDF membrane, as a material conjugated to horseradish peroxidase (HRP). By directly conjugating HRP to the probe, the step of using the antibody (so-called the secondary antibody) to detect the probe can be eliminated.

The hexahistidine-tagged Src SH2 Wt and TrM proteins were purified as described in the above sections, and the tag was cleaved by the Tobacco Etch Virus protease as described in the above sections. The materials were further purified by liquid chromatography using the size exclusion column Superdex75 10/300 (GE Healthcare) in the buffer composed of 0.1 M sodium phosphate and 0.15 M sodium chloride at pH7.2.

400 μl SH2 domain protein at a concentration of 0.3 μg/μl was mixed with the lyophilized activated peroxidise (EZ-Link Plus Activated Peroxidase #31478). Next, 15 μL of freshly prepared SM Sodium Cyanoborohydride was added to the reaction mixture and incubated for 1 hour at room temperature. Next, 30 μL of Quenching Buffer (3M ethanolamine, pH 9) was added for reaction at room temperature for 15 minutes. The HRP-labeled TrMSH2 was dialized against 1 L of pH 7.2 Phosphate Buffered Saline (0.1M sodium phosphate, 0.15M sodium chloride) overnight.

4 μg of the anti-ALK antibody (Santa Cruz) was used to immunoprecipate ALK from 500 μg of H370 cell lysate (treated with or without mAb-46). The immunoprecipitation samples were applied to 8% Bis-Tris SDS-PAGE and the samples were transferred from the SDS-PAGE gel onto two strips of the PVDF membranes. One membrane strip was probed with the TrM SH2-HRP conjugate as 1:500 dilution. For comparison, the other membrane strip was incubated with the primary antibody P-Tyr-100 (Cell Signaling), then anti-mouseIgG secondary antibody-HRP conjugate (Bio-Rad). Signals from the HRP-conjugates on the membranes were detected as enhanced chemiluminescence (Western Lightning Plus-ECL kit, Perkin Elmer) and detected on the x-ray film (FIG. 15B).

Example 13

Detection of Tyrosine-phosphorylated Proteins Using the Src SH2 TrM

Nollau and Mayer (U.S. Pat. No. 7,846,746) demonstrated that SH2 domains can detect a subset of tyrosine-phosphorylated proteins from cell lysate, using the Far-Western blotting method. Because different SH2 domains in nature are equipped with distinct target recognition specificity, each SH2 domain binds to a unique subset of lysate proteins.

Figure 16:
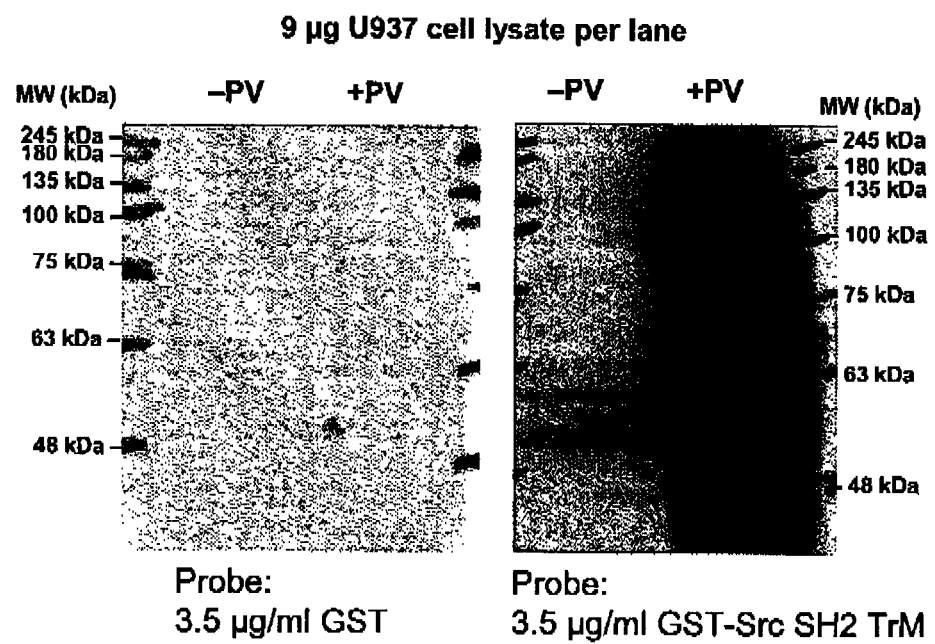
FIG. 16 demonstrates that the Src SH2 TrM can detect tyrosine-phosphorylated proteins on a membrane. The U937 human lymphoma cells were treated with pervanadate (+PV), or without it (−PV, negative control), and 9 μg lysate was loaded on each lane of an SDS-PAGE gel, and transferred to the PVDF membrane (Millipore). GST-Src SH2 TrM bound to phosphorylated proteins on the membrane, and was visualized by rabbit anti-GST antibody-HRP conjugate (Sigma-Aldrich #A7340).

On the contrary, the affinity-enhanced SH2 domain variant binds to a substantially larger portion of phosphorylated proteins in cell lysate. By using the Src SH2 TrM for Far-Western blotting experiments, FIG. 16 demonstrates broad detection of tyrosine-phosphorylated proteins by the SH2 domain variant.

The GST protein and GST-Src SH2 TrM were prepared as 3.5 μg/ml concentration in the TBS buffer (50 mM Tris-HCl pH 7.2, 137 mM NaCl). The cultured U937 cells were treated with or without 50 μM pervanadate in PBS for 10 min at 37° C. The cells were lysed in the buffer (0.5% NP-40, 50 mM HEPES pH 7.4, 1 mM magnesium chloride, 150 mMKCl) with sonication on ice, and supernatant was loaded on an SDS-PAGE gel for separation and following transfer to the PVDF membrane (Millipore). The membrane was blocked with 5% milk in TBS-T (0.5% Tween-20 in TBS) overnight at 4° C., and probed with 3.5 µg/ml GST proteins for 1 hour at room temperature. The membrane was washed with TBS-T, and incubated with anti-GST antibody-HRP (horseradish peroxidase) conjugate (Sigma, #A7340) for 1 hour at room temperature. The signal from HRP was detected as enhanced chemiluminescence on an X-ray film.

Example 14

Monitoring Subcellular Localization of the TrM SH2 Domain to Visualize Tyrosine-phosphorylated Proteins in Live Cells Different from antibody molecules, including phosphotyrosine-specific antibodies, the SH2 variants can be used in live cells as a tool to monitor tyrosine phosphorylation events.

Figure 17:
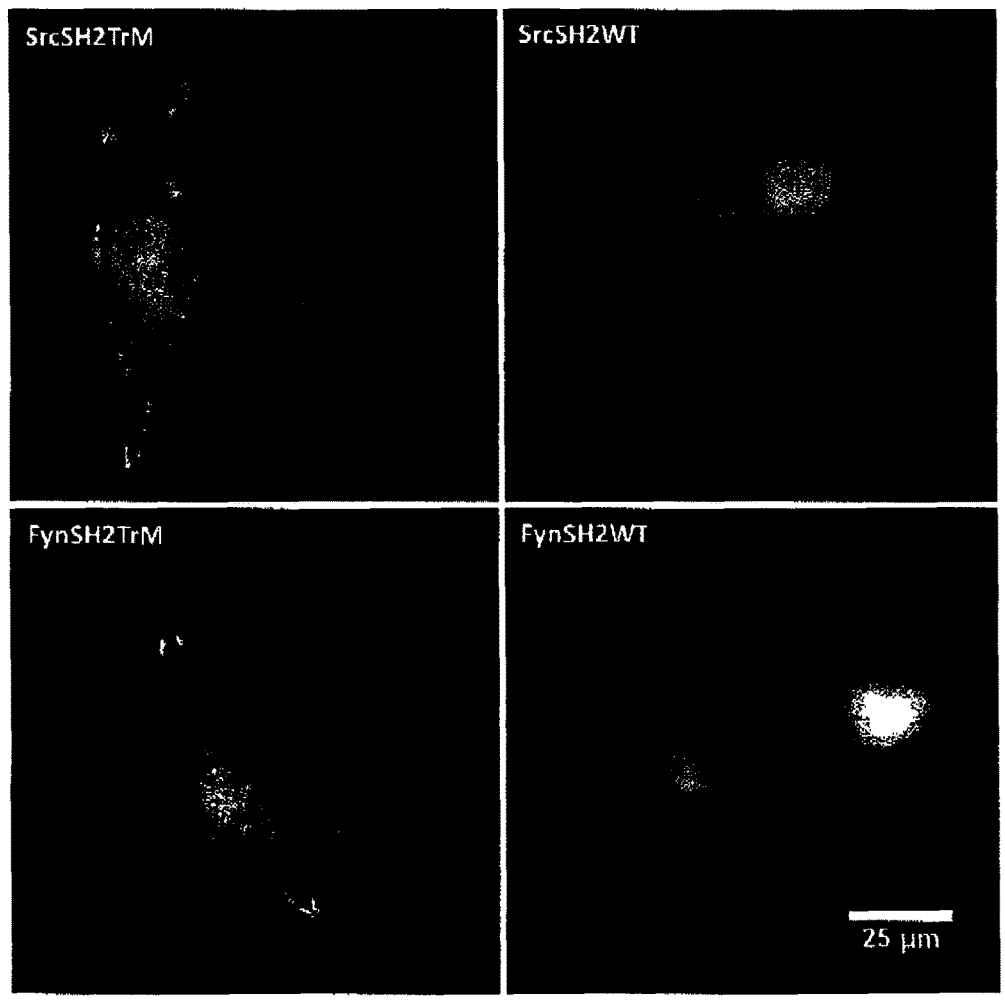
FIG. 17 shows that the Fyn and Src SH2 TrM fused to GFP can be used to monitor localization of tyrosine-phosphorylated proteins in live cells. Images show green fluorescence in A549 cells transfected with GFP-fused TrM SH2 domains or the wild-type (WT) SH2 controls. TrMSrc SH2 and TrM Fyn SH2 domains exhibit similar subcellular localization patterns. In comparison, the WT Src SH2 and Fyn SH2 domains are distributed more or less evenly in the cell with a slight enrichment in the nuclear region. Bar=25 μm for all pictures.

Genes encoding Src SH2 Wt, SrcSH2TrM, FynSH2Wt and FynSH2TrM were inserted into the pEGFP vector (Clontech) to express functional SH2 variants fused with green fluorescent protein. Non-small cell lung cancer cell line A549 were grown in Phenol Red-free Dulbecco's modified Eagle's medium (DMEM; Sigma-Aldrich) supplemented with 10% fetal bovine serum (FBS; SAFC Biosciences), penicillin (50 U/ml), and streptomycin (50 µg/ml) in a humidified atmosphere containing 5% CO$_2$ at 37° C. Cells were transiently transfected by pEGFP constructs with Jet-PEIPolyPlus-transfection according to the manufacturer's protocol. Images were captured in Nikon fluorescent microscope 16 to 20 hours after transfection (FIG. 17).

Example 15

SH2 Variant Selectively Kills EGFR-expressing Cells Under EGF Treatment

Since the TrM SH2 domains inhibited EGFR signaling when the variant SH2 domains were expressed in cells, the variants of the present invention may be used as inhibitors for EGFR signaling. However, the signaling event occurs inside of cells. In order to use the variant SH2 domain as a protein-based inhibitor material, the variant needs to be delivered into cells from the outside of the cell membrane.

Figure 18:
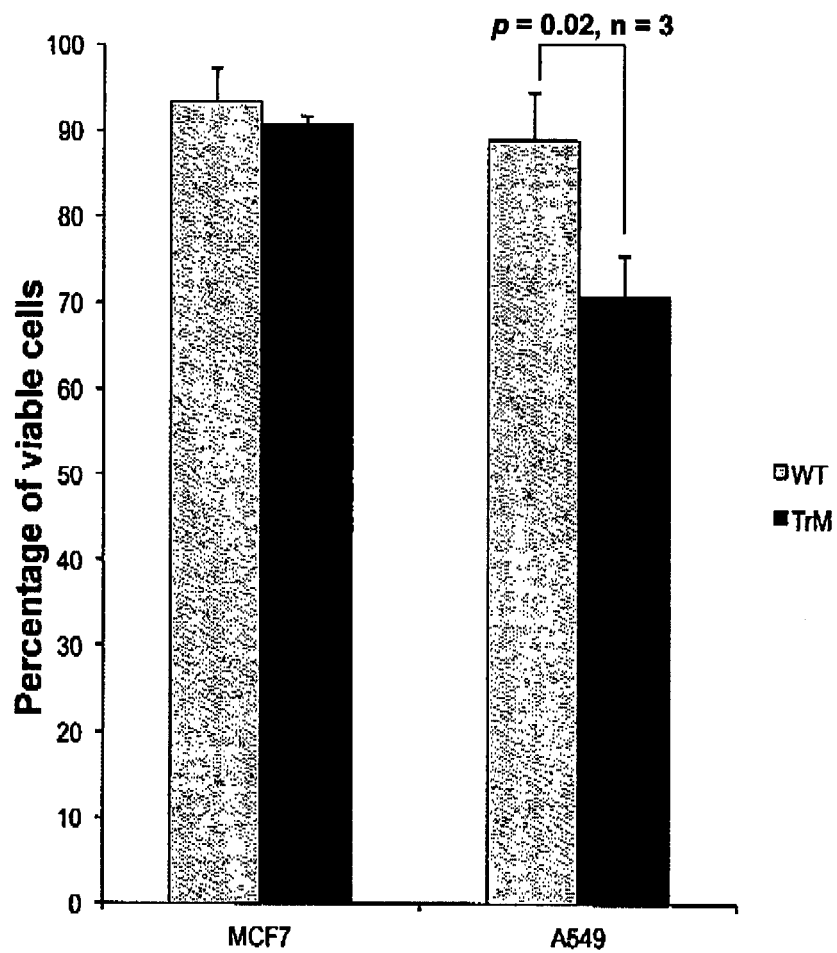
FIG. 18 shows that the recombinant TrMSrc SH2 domain delivered by gold nanoparticles into the A549 cells reduces viability of the cells under the treatment of EGF.

The A549 non-small cell lung cancer cell line expresses a high level of wild-type epidermal growth factor receptor (EGFR) and is suitable for monitoring EGFR activation events (PCT Pub. No. WO/2011/130343). Gold nanoparticles (Zhang et al. Langmuir. 2012 Dec. 11; 28(49):17053-60) were used for delivery of the SH2 variants into cells. FIG. 18 shows that the Src SH2 TrM was delivered into cells and reduced cell variability upon EGF treatment, compared with the Wt SH2 domain. For comparison, MCF-7 cells were also tested for this assay. Since MCF-7 cells do not express the EGF receptor (Ju et al Biochem. J. 2013, 452, 123-134), EGF stimulation did not significantly affect cell variability after SH2 variant delivery (FIG. 18). This result indicates that the TrMSH2 protein exhibits inhibitory effects on cells of which the growth is dependent on EGF.

The hexa-histidine-tagged SrcWt and TrM proteins were purified to homogeneity in 5 mM HEPES buffer (pH 7.6). 1 nM of gold nanoparticle was mixed with 100 nMWt or TrM variant protein. The MCF-7 and A549 cells were starved six hours before treatment. The cells were then treated with 100 ng/ml EGF for 20 hours. The nanoparticle-protein mixture was applied to cells. Cells were trypsinized and stained using 0.4% trypan blue (Sigma-Aldrich) and viable and total cell numbers were counted haemacytometer with the use of a microscope according to manufacturer's instruction.

TABLE 1

| UniProt Database Entry ID | Gene names |
| --- | --- |
| 3BP2_HUMAN | SH3BP2 3BP2 RES4-23 |
| ABL1_HUMAN | ABL1 ABL JTK7 |
| ABL2_HUMAN | ABL2 ABLL ARG |
| BCAR3_HUMAN | BCAR3 NSP2 SH2D3B UNQ271/PRO308 |
| BLK_HUMAN | BLK |
| BLNK_HUMAN | BLNK BASH SLP65 |
| BMX_HUMAN | BMX |
| BTK_HUMAN | BTK AGMX1 ATK BPK |
| CBLB_HUMAN | CBLB RNF56 Nbla00127 |
| CBLC_HUMAN | CBLC CBL3 RNF57 |
| CBL_HUMAN | CBL CBL2 RNF55 |
| CHIN_HUMAN | CHN1 ARHGAP2 CHN |
| CHIO_HUMAN | CHN2 ARHGAP3 BCH |
| CISH_HUMAN | CISH G18 |
| CLNK_HUMAN | CLNK MIST |
| CRKL_HUMAN | CRKL |
| CRK_HUMAN | CRK |
| CSK_HUMAN | CSK |
| DAPP1_HUMAN | DAPP1 BAM32 HSPC066 |
| FER_HUMAN | FER TYK3 |
| FES_HUMAN | FES FPS |
| FGR_HUMAN | FGR SRC2 |
| FRK_HUMAN | FRK PTK5 RAK |
| FYN_HUMAN | FYN |
| GRAP2_HUMAN | GRAP2 GADS GRB2L GRID |
| GRAP_HUMAN | GRAP |
| GRB10_HUMAN | GRB10 GRBIR KIAA0207 |
| GRB14_ HUMAN | GRB14 |
| GRB2_HUMAN | GRB2 ASH |
| GRB7_HUMAN | GRB7 |
| HCK_HUMAN | HCK |
| HSH2D_HUMAN | HSH2D ALX |
| ITK_HUMAN | ITK EMT LYK |
| JAK1_HUMAN | JAK1 JAK1A JAK1B |
| JAK2_HUMAN | JAK2 |
| JAK3_HUMAN | JAK3 |
| KSYK_HUMAN | SYK |
| LCK_HUMAN | LCK |
| LCP2_HUMAN | LCP2 |
| LYN_HUMAN | LYN JTK8 |
| MATK_HUMAN | MATK CTK HYL |
| NCK1_HUMAN | NCK1 NCK |
| NCK2_HUMAN | NCK2 GRB4 |
| P55G_HUMAN | PIK3R3 |
| P85A_HUMAN | PIK3R1 GRB1 |
| P85B_HUMAN | PIK3R2 |
| PLCG1_HUMAN | PLCG1 PLC1 |
| PLCG2_HUMAN | PLCG2 |
| PTK6_HUMAN | PTK6 BRK |
| PTN11_HUMAN | PTPN11 PTP2C SHPTP2 |
| PTN6_HUMAN | PTPN6 HCP PTP1C |
| RASA1_HUMAN | RASA1 RASA |
| RIN1_HUMAN | RIN1 |
| RIN2_HUMAN | RIN2 RASSF4 |
| RIN3_HUMAN | RIN3 |
| SH21A_HUMAN | SH2D1A DSHP SAP |
| SH21B_HUMAN | SH2D1B EAT2 |
| SH22A_HUMAN | SH2D2A SCAP TSAD VRAP |
| SH23A_HUMAN | SH2D3A NSP1 UNQ175/PRO201 |
| SH24A_HUMAN | SH2D4A PPP1R38 SH2A |
| SH24B_HUMAN | SH2D4B |
| SH2B1_HUMAN | SH2B1 KIAA1299 SH2B |
| SH2B2_HUMAN | SH2B2 APS |
| SH2B3_HUMAN | SH2B3 LNK |
| SH2D3_HUMAN | SH2D3C NSP3 UNQ272/PRO309/PRO34088 |
| SH2D5_HUMAN | SH2D5 |
| SH2D6_HUMAN | SH2D6 |

TABLE 1-continued

| UniProt Database Entry ID | Gene names |
| --- | --- |
| SH2D7_HUMAN | SH2D7 |
| SHB_HUMAN | SHB |
| SHC1_HUMAN | SHC1 SHC SHCA |
| SHC2_HUMAN | SHC2 SCK SHCB |
| SHC3_HUMAN | SHC3 NSHC SHCC |
| SHC4_HUMAN | SHC4 SHCD UNQ6438/PRO21364 |
| SHD_HUMAN | SHD |
| SHE_HUMAN | SHE |
| SHF_HUMAN | SHF |
| SHIP1_HUMAN | INPP5D SHIP SHIP1 |
| SHIP2_HUMAN | INPPL1 SHIP2 |
| SLAP1_HUMAN | SLA SLAP SLAP1 |
| SLAP2_HUMAN | SLA2 C20orf156 SLAP2 |
| SOCS1_HUMAN | SOCS1 SSI1 TIP3 |
| SOCS2_HUMAN | SOCS2 CIS2 SSI2 STATI2 |
| SOCS3_HUMAN | SOCS3 CIS3 SSI3 |
| SOCS4_HUMAN | SOCS4 SOCS7 |
| SOCS5_HUMAN | SOCS5 CIS6 CISH5 CISH6 KIAA0671 |
| SOCS6_HUMAN | SOCS6 CIS4 SOCS4 |
| SOCS7_HUMAN | SOCS7 NAP4 SOCS6 |
| SPT6H_HUMAN | SUPT6H KIAA0162 SPT6H |
| SRC_HUMAN | SRC SRC1 |
| SRMS_HUMAN | SRMS C20orf148 |
| STA5A_HUMAN | STAT5A STAT5 |
| STA5B_HUMAN | STAT5B |
| STAP1_HUMAN | STAP1 BRDG1 |
| STAP2_HUMAN | STAP2 BKS |
| STAT1_HUMAN | STAT1 |
| STAT2_HUMAN | STAT2 |
| STAT3_HUMAN | STAT3 APRF |
| STAT4_HUMAN | STAT4 |
| STAT6_HUMAN | STAT6 |
| TEC_HUMAN | TEC PSCTK4 |
| TENC1_HUMAN | TENC1 KIAA1075 TNS2 |
| TENS1_HUMAN | TNS1 TNS |
| TENS3_HUMAN | TNS3 TEM6 TENS1 TPP |
| TENS4_HUMAN | TNS4 CTEN PP14434 |
| TXK_HUMAN | TXK PTK4 RLK |
| TYK2_HUMAN | TYK2 |
| VAV2_HUMAN | VAV2 |
| VAV3_HUMAN | VAV3 |
| VAV_HUMAN | VAV1 VAV |
| YES_HUMAN | YES1 YES |
| ZAP70_HUMAN | ZAP70 SRK |

REFERENCES FOR EXAMPLES 6-10

1. Sierra, J. R., Cepero, V. & Giordano, S. Molecular mechanisms of acquired resistance to tyrosine kinase targeted therapy. *Mol Cancer* 9, 75.
2. Kobayashi, S. et al. An alternative inhibitor overcomes resistance caused by a mutation of the epidermal growth factor receptor. *Cancer Res* 65, 7096-7101 (2005).
3. Kobayashi, S. et al. EGFR mutation and resistance of non-small-cell lung cancer to gefitinib. *N Engl J Med* 352, 786-792 (2005).
4. Zhang, S. et al. Combating trastuzumab resistance by targeting SRC, a common node downstream of multiple resistance pathways. *Nat Med* 17, 461-469 (2011).
5. Grabulovski, D., Kaspar, M. & Neri, D. A novel, non-immunogenic Fyn SH3-derived binding protein with tumor vascular targeting properties. *J. Biol Chem* 282, 3196-3204 (2007).
6. Liu, B. A. et al. The human and mouse complement of SH2 domain proteins-establishing the boundaries of phosphotyrosine signaling. *Molecular Cell* 22, 851-868 (2006).
7. Lappalainen, I., Thusberg, J., Shen, B. & Vihinen, M. Genome wide analysis of pathogenic SH2 domain mutations. *Proteins* 72, 779-792 (2008).
8. Muthuswamy, S. K., Li, D., Lelievre, S., Bissell, M. J. & Brugge, J. S. ErbB2, but not ErbB1, reinitiates proliferation and induces luminal repopulation in epithelial acini. *Nat Cell Biol* 3, 785-792 (2001).
9. Xiang, B. et al. Brk is coamplified with ErbB2 to promote proliferation in breast cancer. *Proc Natl Acad Sci USA* 105, 12463-12468 (2008).
10. Than, L., Xiang, B. & Muthuswamy, S. K. Controlled activation of ErbB1/ErbB2 heterodimers promote invasion of three-dimensional organized epithelia in an ErbB1-dependent manner: implications for progression of ErbB2-overexpressing tumors. *Cancer Res* 66, 5201-5208 (2006).
11. Moulder, S. L. et al. Epidermal growth factor receptor (HER1) tyrosine kinase inhibitor ZD1839 (Iressa) inhibits HER2/neu (erbB2)-overexpressing breast cancer cells in vitro and in vivo. *Cancer Res* 61, 8887-8895 (2001).
12. Aranda, V. et al. Par6-aPKC uncouples ErbB2 induced disruption of polarized epithelial organization from proliferation control. *Nat Cell Biol* 8, 1235-1245 (2006).
13. Kilic, E., Kilic, U. & Hermann, D. M. TAT fusion proteins against ischemic stroke: current status and future perspectives. *Front Biosci* 11, 1716-1721 (2006).
14. Harada, H., Kizaka-Kondoh, S. & Hiraoka, M. Antitumor protein therapy; application of the protein transduction domain to the development of a protein drug for cancer treatment. *Breast Cancer* 13, 16-26 (2006).
15. Arias-Romero, L. E. et al. A Rac-Pak signaling pathway is essential for ErbB2-mediated transformation of human breast epithelial cancer cells. *Oncogene* 29, 5839-5849.
16. Seton-Rogers, S. E. et al. Cooperation of the ErbB2 receptor and transforming growth factor beta in induction of migration and invasion in mammary epithelial cells. *Proc Natl Acad Sci USA* 101, 1257-1262 (2004).
17. Zeller, R. & Rogers, M. Counterstaining and mounting of autoradiographed in situ hybridization slides. *Curr Protoc Mol Biol* Chapter 14, Unit 14 15 (2001).
18. Zhan, L. et al. Deregulation of scribble promotes mammary tumorigenesis and reveals a role for cell polarity in carcinoma. *Cell* 135, 865-878 (2008).
19. Wunderbaldinger, P., Josephson, L. & Weissleder, R. Tat peptide directs enhanced clearance and hepatic permeability of magnetic nanoparticles. *Bioconjug Chem* 13, 264-268 (2002).
20. Saxena, R. & Dwivedi, A. ErbB family receptor inhibitors as therapeutic agents in breast cancer: Current status and future clinical perspective. *Med Res Rev.*
21. Blagoev, B., Ong, S.-E., Kratchmarova, I. & Mann, M. Temporal analysis of phosphotyrosine-dependent signaling networks by quantitative proteomics. *Nat Biotechnol* 22, 1139-1145 (2004).
22. Liu, H. et al. Systematic identification of methyllysine-driven interactions for histone and nonhistone targets. *J Proteome Res* 9, 5827-5836.
23. Ciaccio, M. F., Wagner, J. P., Chuu, C.-P., Lauffenburger, D. A. & Jones, R. B. Systems analysis of EGF receptor signaling dynamics with microwestern arrays. *Nat Methods* 7, 148-155 (2010).

We claim:

1. A variant of an SH2 domain, the variant comprising an amino acid sequence selected from the group consisting of: SEQ ID NOs: 14, 16, 17, 21 and 22.

2. The variant of claim 1, comprising an amino acid sequence selected from the group consisting of: SEQ ID NOs: 17, 21 and 22.

3. The variant of claim 1, comprising SEQ ID NO: 17.

4. The variant of claim 1, comprising SEQ ID NO: 21.

5. The variant of claim 1, comprising SEQ ID NO: 22.

6. The variant of claim 1, comprising SEQ ID NO: 14.

7. The variant of claim 1, comprising SEQ ID NO: 16.

8. A protein comprising at least two SH2 domains, wherein at least one of said at least two SH2 domains is a variant according to claim 1.

9. The protein of claim 8, wherein each of said at least two SH2 domains binds a different pTyr-containing peptide region of a protein that comprises at least two pTyr-containing peptide regions.

* * * * *

SEQUENCE LISTING

<160> NUMBER OF SEQ ID NOS: 27

<210> SEQ ID NO 1
<211> LENGTH: 111
<212> TYPE: PRT
<213> ORGANISM: Homo sapiens
<220> FEATURE:
<221> NAME/KEY: misc_feature
<223> OTHER INFORMATION: FynSH2wt

<400> SEQUENCE: 1

Ala Pro Val Asp Ser Ile Gln Ala Glu Glu Trp Tyr Phe Gly Lys Leu
1               5                   10                  15

Gly Arg Lys Asp Ala Glu Arg Gln Leu Leu Ser Phe Gly Asn Pro Arg
            20                  25                  30

Gly Thr Phe Leu Ile Arg Glu Ser Glu Thr Thr Lys Gly Ala Tyr Ser
        35                  40                  45

Leu Ser Ile Arg Asp Trp Asp Asp Met Lys Gly Asp His Val Lys His
    50                  55                  60

Tyr Lys Ile Arg Lys Leu Asp Asn Gly Gly Tyr Tyr Ile Thr Thr Arg
65                  70                  75                  80

Ala Gln Phe Glu Thr Leu Gln Gln Leu Val Gln His Tyr Ser Glu Arg
                85                  90                  95

Ala Ala Gly Leu Cys Cys Arg Leu Val Val Pro Cys His Lys Gly
            100                 105                 110

<210> SEQ ID NO 2
<211> LENGTH: 333
<212> TYPE: DNA
<213> ORGANISM: Artificial Sequence
<220> FEATURE:
<223> OTHER INFORMATION: Synthetic construct: CyslessFynSH2DNA

<400> SEQUENCE: 2
gctccagttg actctatcca ggcagaagag tggtactttg gaaaacttgg ccgaaaagat      60
gctgagcgac agctattgtc ctttggaaac ccaagaggta cctttcttat ccgcgagagt     120
gaaaccacca aggtgcccta ttcactttct atccgtgatt gggatgatat gaaaggagac     180
catgtcaaac attataaaat tcgcaaactt gacaatggtg atactacat accacccgg      240 gcccagtttg aaacacttca gcagcttgta caacattact cagagagagc tgcaggtctc     300
tcctcccgcc tagtagttcc ctctcacaaa ggg                                  333

<210> SEQ ID NO 3
<211> LENGTH: 111
<212> TYPE: PRT
<213> ORGANISM: Artificial Sequence
<220> FEATURE:
<223> OTHER INFORMATION: Synthetic construct: CyslessFynSH2Protein

<400> SEQUENCE: 3

Ala Pro Val Asp Ser Ile Gln Ala Glu Glu Trp Tyr Phe Gly Lys Leu
1               5                   10                  15

Gly Arg Lys Asp Ala Glu Arg Gln Leu Leu Ser Phe Gly Asn Pro Arg
            20                  25                  30

Gly Thr Phe Leu Ile Arg Glu Ser Glu Thr Thr Lys Gly Ala Tyr Ser
        35                  40                  45

Leu Ser Ile Arg Asp Trp Asp Asp Met Lys Gly Asp His Val Lys His
    50                  55                  60

Tyr Lys Ile Arg Lys Leu Asp Asn Gly Gly Tyr Tyr Ile Thr Thr Arg

```
                65                  70                  75                  80
Ala Gln Phe Glu Thr Leu Gln Gln Leu Val Gln His Tyr Ser Glu Arg
                    85                  90                  95

Ala Ala Gly Leu Ser Ser Arg Leu Val Val Pro Ser His Lys Gly
                100                 105                 110

<210> SEQ ID NO 4
<211> LENGTH: 142
<212> TYPE: PRT
<213> ORGANISM: Artificial Sequence
<220> FEATURE:
<223> OTHER INFORMATION: Synthetic construct: HisTagCyslessFynSH2

<400> SEQUENCE: 4

Met Lys Ile Glu Glu His His His His His His Ser Ser Gly Arg Glu
1               5                   10                  15

Asn Leu Tyr Phe Gln Gly Gly Ala Ala Gln Pro Ala Ala Pro Val Asp
                20                  25                  30

Ser Ile Gln Ala Glu Glu Trp Tyr Phe Gly Lys Leu Gly Arg Lys Asp
            35                  40                  45

Ala Glu Arg Gln Leu Leu Ser Phe Gly Asn Pro Arg Gly Thr Phe Leu
        50                  55                  60

Ile Arg Glu Ser Glu Thr Thr Lys Gly Ala Tyr Ser Leu Ser Ile Arg
65                  70                  75                  80

Asp Trp Asp Asp Met Lys Gly Asp His Val Lys His Tyr Lys Ile Arg
                85                  90                  95

Lys Leu Asp Asn Gly Gly Tyr Tyr Ile Thr Thr Arg Ala Gln Phe Glu
                100                 105                 110

Thr Leu Gln Gln Leu Val Gln His Tyr Ser Glu Arg Ala Ala Gly Leu
            115                 120                 125

Ser Ser Arg Leu Val Val Pro Ser His Lys Gly Ala Ala Ala
        130                 135                 140

<210> SEQ ID NO 5
<211> LENGTH: 49
<212> TYPE: PRT
<213> ORGANISM: Artificial Sequence
<220> FEATURE:
<223> OTHER INFORMATION: Synthetic construct: T8V

<400> SEQUENCE: 5

Arg Lys Asp Ala Glu Arg Gln Leu Leu Ser Phe Gly Asn Pro Arg Gly
1               5                   10                  15

Thr Phe Leu Ile Arg Glu Ser Glu Thr Val Lys Gly Ala Tyr Ser Leu
                20                  25                  30

Ser Ile Arg Asp Trp Asp Asp Met Lys Gly Asp His Val Lys His Tyr
            35                  40                  45

Lys

<210> SEQ ID NO 6
<211> LENGTH: 49
<212> TYPE: PRT
<213> ORGANISM: Artificial Sequence
<220> FEATURE:
<223> OTHER INFORMATION: Synthetic construct: S10V

<400> SEQUENCE: 6

Arg Lys Asp Ala Glu Arg Gln Leu Leu Ser Phe Gly Asn Pro Arg Gly
1               5                   10                  15
```

```
Thr Phe Leu Ile Arg Glu Ser Glu Thr Lys Gly Ala Tyr Val Leu
            20                  25                  30

Ser Ile Arg Asp Trp Asp Asp Met Lys Gly Asp His Val Lys His Tyr
        35                  40                  45

Lys

<210> SEQ ID NO 7
<211> LENGTH: 48
<212> TYPE: PRT
<213> ORGANISM: Artificial Sequence
<220> FEATURE:
<223> OTHER INFORMATION: Synthetic construct: deltaT8/S10A/K15L

<400> SEQUENCE: 7

Arg Lys Asp Ala Glu Arg Gln Leu Leu Ser Phe Gly Asn Pro Arg Gly
1               5                   10                  15

Thr Phe Leu Ile Arg Glu Ser Glu Thr Lys Gly Ala Tyr Ala Leu Ser
            20                  25                  30

Ile Arg Asp Trp Asp Asp Met Lys Gly Asp His Val Lys His Tyr Leu
        35                  40                  45

<210> SEQ ID NO 8
<211> LENGTH: 49
<212> TYPE: PRT
<213> ORGANISM: Artificial Sequence
<220> FEATURE:
<223> OTHER INFORMATION: Synthetic construct: S10A

<400> SEQUENCE: 8

Arg Lys Asp Ala Glu Arg Gln Leu Leu Ser Phe Gly Asn Pro Arg Gly
1               5                   10                  15

Thr Phe Leu Ile Arg Glu Ser Glu Thr Thr Lys Gly Ala Tyr Ala Leu
            20                  25                  30

Ser Ile Arg Asp Trp Asp Asp Met Lys Gly Asp His Val Lys His Tyr
        35                  40                  45

Lys

<210> SEQ ID NO 9
<211> LENGTH: 49
<212> TYPE: PRT
<213> ORGANISM: Artificial Sequence
<220> FEATURE:
<223> OTHER INFORMATION: Synthetic construct: K15L

<400> SEQUENCE: 9

Arg Lys Asp Ala Glu Arg Gln Leu Leu Ser Phe Gly Asn Pro Arg Gly
1               5                   10                  15

Thr Phe Leu Ile Arg Glu Ser Glu Thr Thr Lys Gly Ala Tyr Ser Leu
            20                  25                  30

Ser Ile Arg Asp Trp Asp Asp Met Lys Gly Asp His Val Lys His Tyr
        35                  40                  45

Leu

<210> SEQ ID NO 10
<211> LENGTH: 49
<212> TYPE: PRT
<213> ORGANISM: Artificial Sequence
<220> FEATURE:
<223> OTHER INFORMATION: Synthetic construct: S10V/K15L

<400> SEQUENCE: 10
```

-continued

Arg Lys Asp Ala Glu Arg Gln Leu Leu Ser Phe Gly Asn Pro Arg Gly
1               5                   10                  15

Thr Phe Leu Ile Arg Glu Ser Glu Thr Thr Lys Gly Ala Tyr Val Leu
            20                  25                  30

Ser Ile Arg Asp Trp Asp Asp Met Lys Gly Asp His Val Lys His Tyr
        35                  40                  45

Leu

<210> SEQ ID NO 11
<211> LENGTH: 49
<212> TYPE: PRT
<213> ORGANISM: Artificial Sequence
<220> FEATURE:
<223> OTHER INFORMATION: Synthetic construct: K2E/T8V/S10A/K15I

<400> SEQUENCE: 11

Arg Glu Asp Ala Glu Arg Gln Leu Leu Ser Phe Gly Asn Pro Arg Gly
1               5                   10                  15

Thr Phe Leu Ile Arg Glu Ser Glu Thr Val Lys Gly Ala Tyr Ala Leu
            20                  25                  30

Ser Ile Arg Asp Trp Asp Asp Met Lys Gly Asp His Val Lys His Tyr
        35                  40                  45

Ile

<210> SEQ ID NO 12
<211> LENGTH: 49
<212> TYPE: PRT
<213> ORGANISM: Artificial Sequence
<220> FEATURE:
<223> OTHER INFORMATION: Synthetic construct: T7S/S10A/K15L

<400> SEQUENCE: 12

Arg Lys Asp Ala Glu Arg Gln Leu Leu Ser Phe Gly Asn Pro Arg Gly
1               5                   10                  15

Thr Phe Leu Ile Arg Glu Ser Glu Ser Thr Lys Gly Ala Tyr Ala Leu
            20                  25                  30

Ser Ile Arg Asp Trp Asp Asp Met Lys Gly Asp His Val Lys His Tyr
        35                  40                  45

Leu

<210> SEQ ID NO 13
<211> LENGTH: 49
<212> TYPE: PRT
<213> ORGANISM: Artificial Sequence
<220> FEATURE:
<223> OTHER INFORMATION: Synthetic construct: S10A/K15L

<400> SEQUENCE: 13

Arg Lys Asp Ala Glu Arg Gln Leu Leu Ser Phe Gly Asn Pro Arg Gly
1               5                   10                  15

Thr Phe Leu Ile Arg Glu Ser Glu Thr Thr Lys Gly Ala Tyr Ala Leu
            20                  25                  30

Ser Ile Arg Asp Trp Asp Asp Met Lys Gly Asp His Val Lys His Tyr
        35                  40                  45

Leu

<210> SEQ ID NO 14
<211> LENGTH: 111
<212> TYPE: PRT
<213> ORGANISM: Artificial Sequence

```
<220> FEATURE:
<223> OTHER INFORMATION: Synthetic construct: T8V/S10A/K15I

<400> SEQUENCE: 14

Ala Pro Val Asp Ser Ile Gln Ala Glu Glu Trp Tyr Phe Gly Lys Leu
1               5                   10                  15

Gly Arg Lys Asp Ala Glu Arg Gln Leu Leu Ser Phe Gly Asn Pro Arg
            20                  25                  30

Gly Thr Phe Leu Ile Arg Glu Ser Glu Thr Val Lys Gly Ala Tyr Ala
        35                  40                  45

Leu Ser Ile Arg Asp Trp Asp Asp Met Lys Gly Asp His Val Lys His
    50                  55                  60

Tyr Ile Ile Arg Lys Leu Asp Asn Gly Gly Tyr Tyr Ile Thr Thr Arg
65                  70                  75                  80

Ala Gln Phe Glu Thr Leu Gln Gln Leu Val Gln His Tyr Ser Glu Arg
            85                  90                  95

Ala Ala Gly Leu Cys Cys Arg Leu Val Val Pro Cys His Lys Gly
        100                 105                 110

<210> SEQ ID NO 15
<211> LENGTH: 49
<212> TYPE: PRT
<213> ORGANISM: Artificial Sequence
<220> FEATURE:
<223> OTHER INFORMATION: Synthetic construct: T8V/K15L

<400> SEQUENCE: 15

Arg Lys Asp Ala Glu Arg Gln Leu Leu Ser Phe Gly Asn Pro Arg Gly
1               5                   10                  15

Thr Phe Leu Ile Arg Glu Ser Glu Thr Val Lys Gly Ala Tyr Ser Leu
            20                  25                  30

Ser Ile Arg Asp Trp Asp Asp Met Lys Gly Asp His Val Lys His Tyr
        35                  40                  45

Leu

<210> SEQ ID NO 16
<211> LENGTH: 111
<212> TYPE: PRT
<213> ORGANISM: Artificial Sequence
<220> FEATURE:
<223> OTHER INFORMATION: Synthetic construct: T8I/S10A/K15L

<400> SEQUENCE: 16

Ala Pro Val Asp Ser Ile Gln Ala Glu Glu Trp Tyr Phe Gly Lys Leu
1               5                   10                  15

Gly Arg Lys Asp Ala Glu Arg Gln Leu Leu Ser Phe Gly Asn Pro Arg
            20                  25                  30

Gly Thr Phe Leu Ile Arg Glu Ser Glu Thr Ile Lys Gly Ala Tyr Ala
        35                  40                  45

Leu Ser Ile Arg Asp Trp Asp Asp Met Lys Gly Asp His Val Lys His
    50                  55                  60

Tyr Leu Ile Arg Lys Leu Asp Asn Gly Gly Tyr Tyr Ile Thr Thr Arg
65                  70                  75                  80

Ala Gln Phe Glu Thr Leu Gln Gln Leu Val Gln His Tyr Ser Glu Arg
            85                  90                  95

Ala Ala Gly Leu Cys Cys Arg Leu Val Val Pro Cys His Lys Gly
        100                 105                 110
```

<210> SEQ ID NO 17
<211> LENGTH: 111
<212> TYPE: PRT
<213> ORGANISM: Artificial Sequence
<220> FEATURE:
<223> OTHER INFORMATION: Synthetic construct: T8V/S10A/K15L

<400> SEQUENCE: 17

```
Ala Pro Val Asp Ser Ile Gln Ala Glu Glu Trp Tyr Phe Gly Lys Leu
1               5                   10                  15

Gly Arg Lys Asp Ala Glu Arg Gln Leu Leu Ser Phe Gly Asn Pro Arg
            20                  25                  30

Gly Thr Phe Leu Ile Arg Glu Ser Glu Thr Val Lys Gly Ala Tyr Ala
        35                  40                  45

Leu Ser Ile Arg Asp Trp Asp Asp Met Lys Gly Asp His Val Lys His
    50                  55                  60

Tyr Leu Ile Arg Lys Leu Asp Asn Gly Gly Tyr Tyr Ile Thr Thr Arg
65                  70                  75                  80

Ala Gln Phe Glu Thr Leu Gln Gln Leu Val Gln His Tyr Ser Glu Arg
                85                  90                  95

Ala Ala Gly Leu Cys Cys Arg Leu Val Val Pro Cys His Lys Gly
            100                 105                 110
```

<210> SEQ ID NO 18
<211> LENGTH: 136
<212> TYPE: PRT
<213> ORGANISM: Artificial Sequence
<220> FEATURE:
<223> OTHER INFORMATION: Synthetic construct: HisTagSrcSH2wt

<400> SEQUENCE: 18

```
Met Lys His His His His His His Pro Met Ser Asp Tyr Asp Ile Pro
1               5                   10                  15

Thr Thr Glu Asn Leu Tyr Phe Gln Gly Ala Met Asp Ser Ile Gln Ala
            20                  25                  30

Glu Glu Trp Tyr Phe Gly Lys Ile Thr Arg Arg Glu Ser Glu Arg Leu
        35                  40                  45

Leu Leu Asn Ala Glu Asn Pro Arg Gly Thr Phe Leu Val Arg Glu Ser
    50                  55                  60

Glu Thr Thr Lys Gly Ala Tyr Cys Leu Ser Val Ser Asp Phe Asp Asn
65                  70                  75                  80

Ala Lys Gly Leu Asn Val Lys His Tyr Lys Ile Arg Lys Leu Asp Ser
                85                  90                  95

Gly Gly Phe Tyr Ile Thr Ser Arg Thr Gln Phe Asn Ser Leu Gln Gln
            100                 105                 110

Leu Val Ala Tyr Tyr Ser Lys His Ala Asp Gly Leu Cys His Arg Leu
        115                 120                 125

Thr Thr Val Cys Pro Thr Ser Lys
    130                 135
```

<210> SEQ ID NO 19
<211> LENGTH: 24
<212> TYPE: PRT
<213> ORGANISM: Artificial Sequence
<220> FEATURE:
<223> OTHER INFORMATION: Synthetic construct: K15L

<400> SEQUENCE: 19

```
Thr Lys Gly Ala Tyr Cys Leu Ser Val Ser Asp Phe Asp Asn Ala Lys
1               5                   10                  15
```

Gly Leu Asn Val Lys His Tyr Leu
            20

<210> SEQ ID NO 20
<211> LENGTH: 24
<212> TYPE: PRT
<213> ORGANISM: Artificial Sequence
<220> FEATURE:
<223> OTHER INFORMATION: Synthetic construct: T8V/C10A

<400> SEQUENCE: 20

Val Lys Gly Ala Tyr Ala Leu Ser Val Ser Asp Phe Asp Asn Ala Lys
1               5                   10                  15

Gly Leu Asn Val Lys His Tyr Lys
            20

<210> SEQ ID NO 21
<211> LENGTH: 109
<212> TYPE: PRT
<213> ORGANISM: Artificial Sequence
<220> FEATURE:
<223> OTHER INFORMATION: Synthetic construct: T8V/C10A/K15L

<400> SEQUENCE: 21

Asp Ser Ile Gln Ala Glu Glu Trp Tyr Phe Gly Lys Ile Thr Arg Arg
1               5                   10                  15

Glu Ser Glu Arg Leu Leu Leu Asn Ala Glu Asn Pro Arg Gly Thr Phe
            20                  25                  30

Leu Val Arg Glu Ser Glu Thr Val Lys Gly Ala Tyr Ala Leu Ser Val
        35                  40                  45

Ser Asp Phe Asp Asn Ala Lys Gly Leu Asn Val Lys His Tyr Leu Ile
    50                  55                  60

Arg Lys Leu Asp Ser Gly Gly Phe Tyr Ile Thr Ser Arg Thr Gln Phe
65                  70                  75                  80

Asn Ser Leu Gln Gln Leu Val Ala Tyr Tyr Ser Lys His Ala Asp Gly
                85                  90                  95

Leu Cys His Arg Leu Thr Thr Val Cys Pro Thr Ser Lys
            100                 105

<210> SEQ ID NO 22
<211> LENGTH: 104
<212> TYPE: PRT
<213> ORGANISM: Artificial Sequence
<220> FEATURE:
<223> OTHER INFORMATION: Synthetic construct: Grb2_triple

<400> SEQUENCE: 22

Met Lys Pro His Pro Trp Phe Phe Gly Lys Ile Pro Arg Ala Lys Ala
1               5                   10                  15

Glu Glu Met Leu Ser Lys Gln Arg His Asp Gly Ala Phe Leu Ile Arg
            20                  25                  30

Glu Ser Glu Ser Val Pro Gly Asp Phe Ala Leu Ser Val Lys Phe Gly
        35                  40                  45

Asn Asp Val Gln His Phe Leu Val Leu Arg Asp Gly Ala Gly Lys Tyr
    50                  55                  60

Phe Leu Trp Val Val Lys Phe Asn Ser Leu Asn Glu Leu Val Asp Tyr
65                  70                  75                  80

His Arg Ser Thr Ser Val Ser Arg Asn Gln Gln Ile Phe Leu Arg Asp
                85                  90                  95

Ile Glu Gln Val Pro Gln Gln Pro
            100

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide: fluorescein-GGpYGG peptide
<220> FEATURE:
<221> NAME/KEY: MOD_RES
<222> LOCATION: (3)..(3)
<223> OTHER INFORMATION: PHOSPHORYLATION

<400> SEQUENCE: 23

Gly Gly Tyr Gly Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide: non-phosphorylated
      fluorescein-GGYGG peptide

<400> SEQUENCE: 24

Gly Gly Tyr Gly Gly
1               5

<210> SEQ ID NO 25
<211> LENGTH: 11
<212> TYPE: PRT
<213> ORGANISM: Artificial Sequence
<220> FEATURE:
<223> OTHER INFORMATION: Synthetic peptide

<400> SEQUENCE: 25

Ser Ser Arg Leu Val Val Pro Ser His Lys Gly
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic peptide

<400> SEQUENCE: 26

Ser Ser Arg Leu Val Val Pro Ser His Lys Gly Ala Ala Ala
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide: FLAG tag sequence

<400> SEQUENCE: 27

Asp Tyr Lys Asp Asp Asp Asp Lys Cys
1               5